US010281482B2

(12) United States Patent
Fagrell et al.

(10) Patent No.: US 10,281,482 B2
(45) Date of Patent: May 7, 2019

(54) NON-MODAL INTERPLATE MICROWAVE HEATING SYSTEM AND METHOD OF HEATING

(71) Applicant: Dako Denmark A/S, Glostrup (DK)

(72) Inventors: Magnus Fagrell, Uppsala (SE); Ian Christopher Ray, Danderyd (SE)

(73) Assignee: DAKO DENMARK A/S, Glostrup (DK)

( * ) Notice: Subject to any disclaimer, the term of this patent is extended or adjusted under 35 U.S.C. 154(b) by 637 days.

(21) Appl. No.: 14/940,859

(22) Filed: Nov. 13, 2015

(65) Prior Publication Data
US 2016/0252538 A1  Sep. 1, 2016

Related U.S. Application Data

(62) Division of application No. 12/968,467, filed on Dec. 15, 2010.
(60) Provisional application No. 61/286,917, filed on Dec. 16, 2009.

(51) Int. Cl.
| | | |
|---|---|---|
| H05B 6/54 | (2006.01) | |
| H05B 6/72 | (2006.01) | |
| G01N 35/02 | (2006.01) | |
| H05B 6/46 | (2006.01) | |
| H05B 6/80 | (2006.01) | |
| G01N 1/30 | (2006.01) | |
| G01N 35/00 | (2006.01) | |

(52) U.S. Cl.
CPC ............ *G01N 35/026* (2013.01); *G01N 1/30* (2013.01); *G01N 35/0099* (2013.01); *H05B 6/46* (2013.01); *H05B 6/80* (2013.01); *H05B 6/806* (2013.01)

(58) Field of Classification Search
CPC . H05B 6/46; H05B 6/806; H05B 6/80; G01N 1/30; G01N 35/0099; G01N 35/026
USPC ....... 219/702, 651, 770, 775, 762, 776, 774, 219/748, 750, 756; 422/22; 435/6.11
See application file for complete search history.

(56) References Cited

U.S. PATENT DOCUMENTS

| | | |
|---|---|---|
| 3,221,132 A | 11/1965 | Staats |
| 4,099,042 A | 7/1978 | Jean et al. |
| 4,978,501 A | 12/1990 | Diprose et al. |
| 5,289,140 A | 2/1994 | Jorgenson et al. |
| 5,641,423 A | 6/1997 | Bridges et al. |
| 6,097,015 A * | 8/2000 | McCullough ............ A61L 2/12 219/686 |

(Continued)

FOREIGN PATENT DOCUMENTS

| | | |
|---|---|---|
| GB | 2457494 | 8/2008 |
| JP | 2004-360964 | 12/2004 |

(Continued)

OTHER PUBLICATIONS

Office Action dated Sep. 19, 2017 for Canadian Patent Application No. 2,782,894 (4 pages).

(Continued)

*Primary Examiner* — Quang T Van

(57) ABSTRACT

A microwave heater and a method of heating are provided. The microwave heater includes a non-modal interplate microwave applicator and may include a nonresonant enclosure. The non-modal interplate microwave applicator is configured to receive therein a load to be heated by microwaves radiated from the non-modal interplate microwave applicator.

16 Claims, 36 Drawing Sheets

(56) References Cited

U.S. PATENT DOCUMENTS

| | | |
|---|---|---|
| 6,350,973 B2 | 2/2002 | Wroe et al. |
| 6,949,370 B1 * | 9/2005 | Barany .................... C12N 9/93 |
| | | 435/183 |
| 2003/0205571 A1 | 11/2003 | Flugstad et al. |
| 2004/0209303 A1 | 10/2004 | Martin |

FOREIGN PATENT DOCUMENTS

| | | |
|---|---|---|
| JP | 2006-501050 | 1/2006 |
| WO | 0119963 A2 | 3/2001 |
| WO | 2008/030337 | 3/2008 |

OTHER PUBLICATIONS

Japanese Patent Office, Office Action for application 2012-543474, dated Feb. 3, 2015, 3 pages.
Partial International Search Report for PCT/DK2010/000178, International Search Authority, dated Apr. 21, 2011, 5 pages.
Yoshino Koji et al., High Frequency heating cooker, Translation of JP2004360964A on Jun. 23, 2015.

* cited by examiner

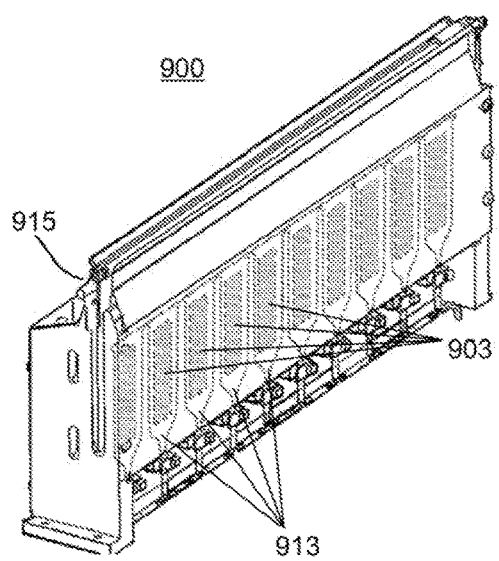
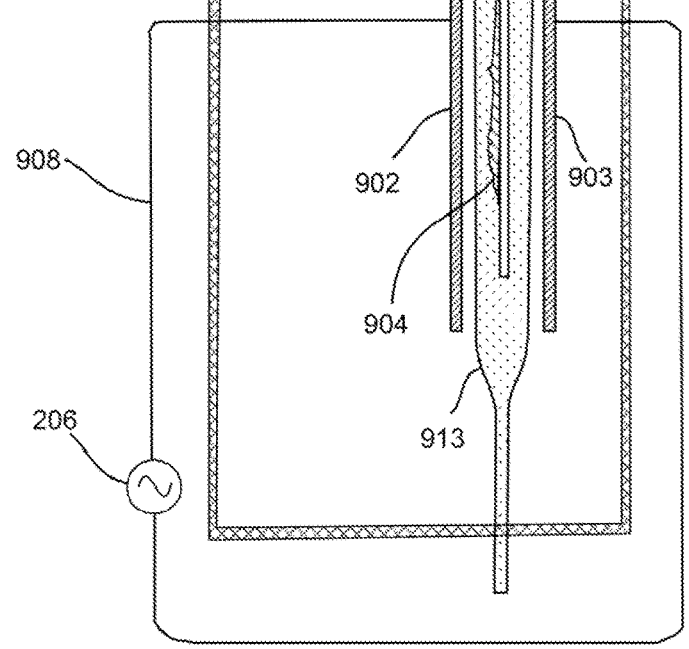
Fig. 9A
Fig. 9B

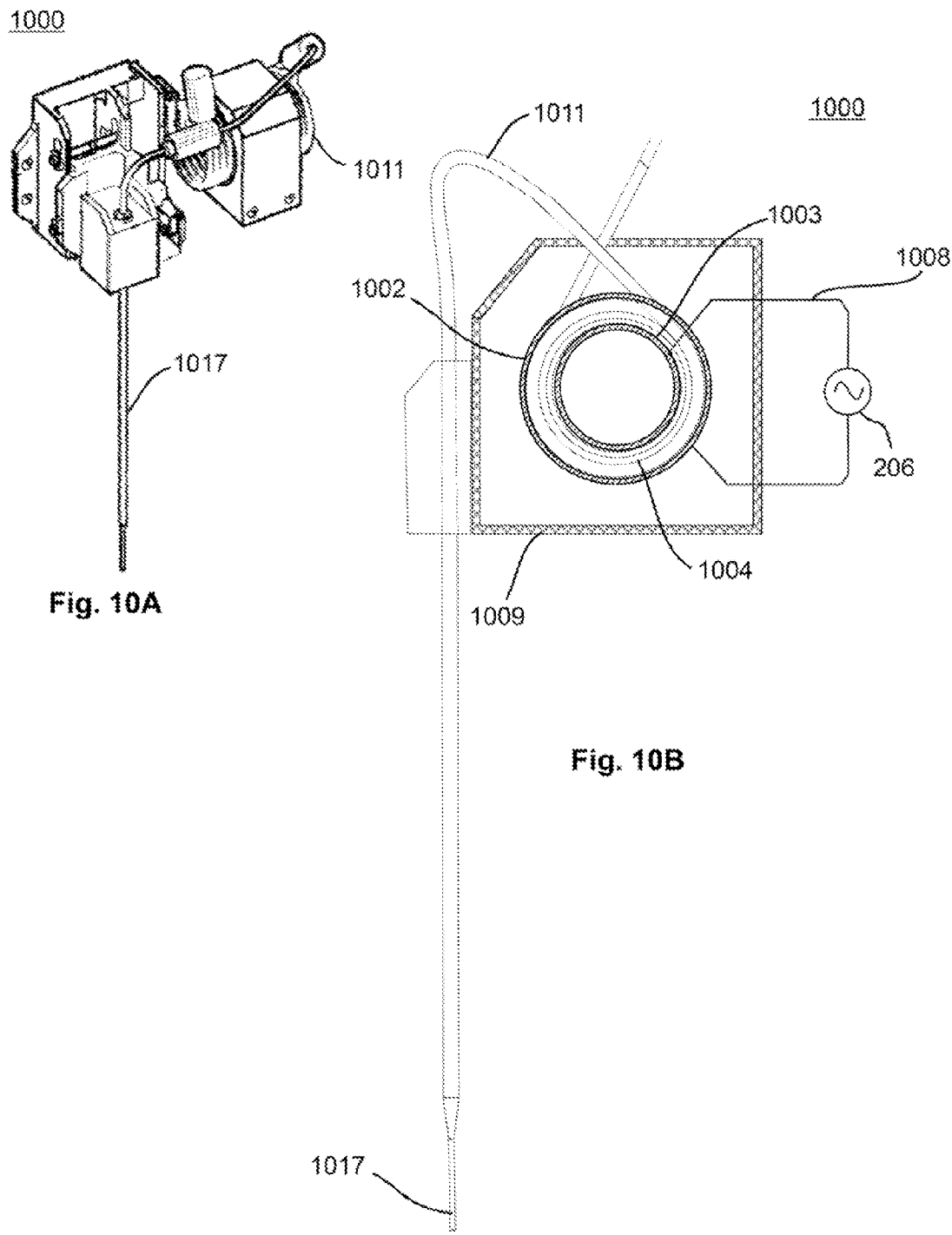

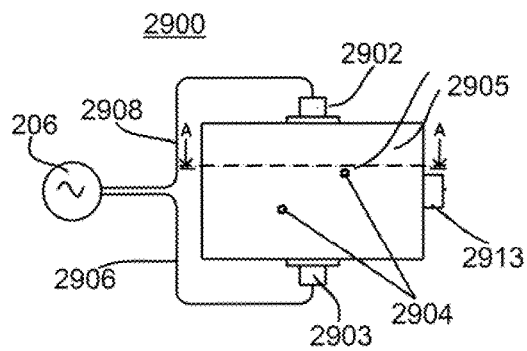
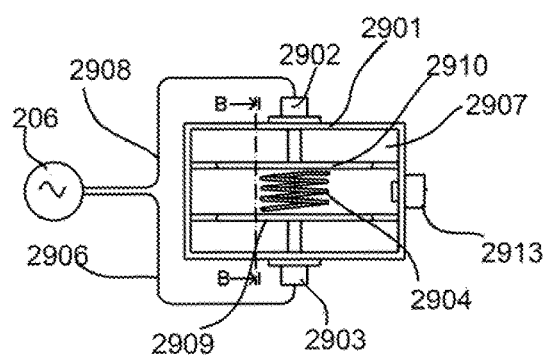
Fig. 29A                               Fig. 29B
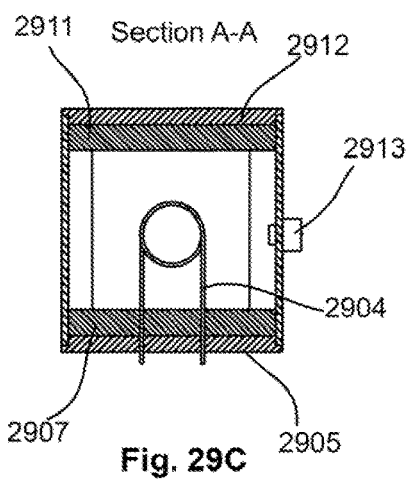
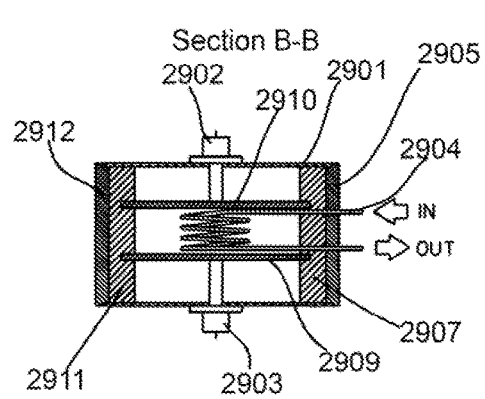
Fig. 29C                               Fig. 29D
Fig. 29E                               Fig. 29F

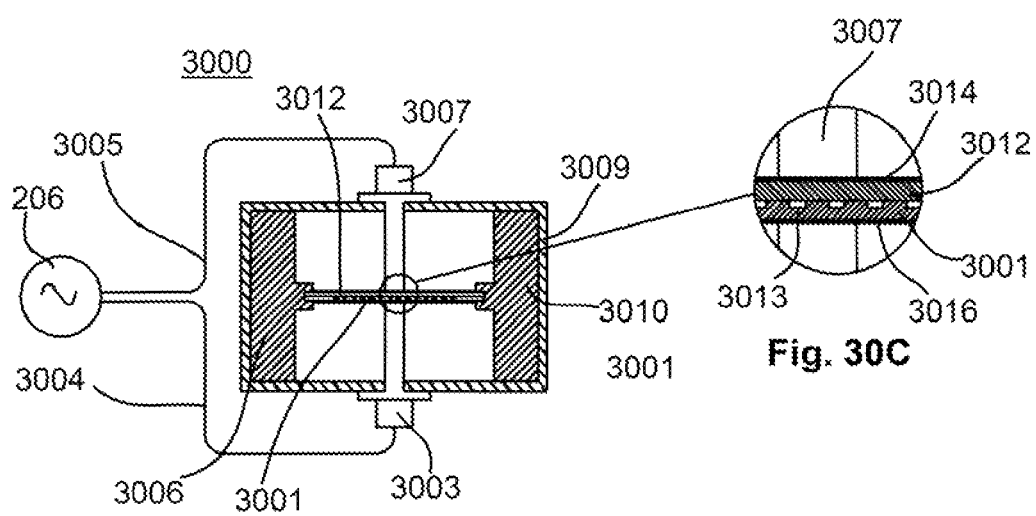
Fig. 30A
Fig. 30C
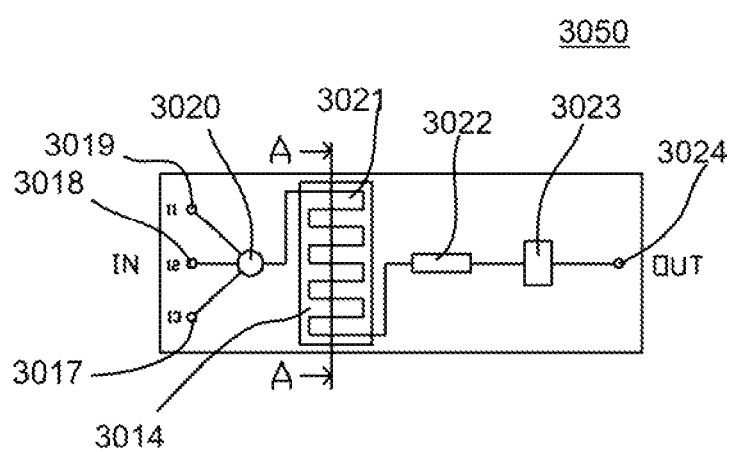
Fig. 30B

NON-MODAL INTERPLATE MICROWAVE HEATING SYSTEM AND METHOD OF HEATING

This is a continuation of U.S. patent application Ser. No. 12/968,467, filed Dec. 15, 2010 (published on Jun. 16, 2011 as Publication No. 2011/0139773), which claims the benefit of U.S. Provisional Patent Application No. 61/286,917, filed Dec. 16, 2009, all of which are incorporated herein by reference in their entirety.

FIELD OF THE INVENTION

The present disclosure relates to microwave heating systems and, more particularly, to microwave applicators for heating diagnostic tissue specimens and reagents and methods of heating specimens.

BACKGROUND OF THE INVENTION

A microwave applicator employs microwave radiation to heat an object. Microwave applicators may be used in many different applications ranging from home or personal use for heating foods, to commercial or industrial uses.

Efforts have been made to adapt microwave ovens designed for domestic kitchen use for use in laboratory specimen and reagent heating. Multi-mode microwave systems including those designed for domestic use and commercial laboratory use exist. Further, single-mode microwave systems have been designed for laboratory and industrial use. Both multi-mode and single mode microwave system rely on a resonant cavity and modal microwaves. However, such devices have inherent disadvantages and limitations which may include: uneven specimen heating due to the variation of microwave energy density within the mode patterns, bulkiness due in part to the requirement for a resonant cavity, complexity in order to control or compensate for variation in energy density with the field to be heated, imprecision, unsuitability for processing single specimens or small groups of specimen, troublesome constraints on specimen orientation and placement, power and voltage requirements, excess heat generation, requirement to use a fixed microwave frequency, and high cost.

Therefore there has been a need for a type of microwave applicator that overcomes the disadvantages and limitations of existing multi-mode and single-mode microwave systems.

SUMMARY OF THE INVENTION

An embodiment of the invention may comprise a microwave heating system comprising: a non-modal interplate microwave applicator configured to receive a load to be heated by microwaves radiated from the applicator; and a microwave source connected to the non-modal interplate microwave applicator.

An embodiment of the invention may comprise a microwave heating system comprising: a non-modal interplate microwave applicator configured to receive a load to be heated by microwaves radiated from the applicator; a microwave source connected to the non-modal interplate microwave applicator; and a nonresonant enclosure that at least partially encloses the non-modal interplate microwave applicator.

An embodiment of the invention may comprise a microwave heating system comprising: a non-modal interplate microwave applicator configured to receive a load to be heated by microwaves radiated from the applicator; a microwave source connected to the non-modal interplate microwave applicator; a nonresonant enclosure that at least partially encloses the non-modal interplate microwave applicator; and a supporting structure in combination with the non-modal interplate microwave applicator for maintaining the load within the non-modal interplate microwave applicator.

An embodiment of the invention may comprise a method for heating a load with microwaves, the method comprising: forming a non-modal interplate microwave applicator shaped to define an applicator for generating an electromagnetic field therein; and configuring the non-modal interplate microwave applicator to generate the electromagnetic field within a nonresonant structure to heat a load using microwaves.

BRIEF DESCRIPTION OF THE DRAWINGS

FIGS. 9A-9B are illustrations of single piece diptanks with individual non-modal interplate microwave applicators.

FIGS. 10A-10B are illustrations of a cylindrical non-modal interplate microwave applicator enclosing a length of wound tubing.

FIGS. 29A-29F are illustrations of embodiments of a non-modal interplate microware applicator that includes capillary tubing type flow reactors.

FIGS. 30A-30C are illustrations of an embodiment of a non-modal interplate microwave applicator that includes a microstructure with inputs; a mixing chamber; a heating portion; a separation portion; an analysis portion; and an output portion.

DETAILED DESCRIPTION OF THE EMBODIMENTS

The various embodiments of the invention presented herein illustrate how to practice the invention and the various advantages the invention has over existing methods.

By directly heating a load using a non-modal interplate microwave applicator as described herein or equivalent variations thereof, a number of beneficial effects may be achieved including that the non-modal interplate microwave applicator may be made very small, it may require only a very low power while providing uniform, well-controlled heating of loads positioned between the plates; the non-modal interplate microwave applicator may be formed automatically by bringing the plates together automatically which enables a load to be inserted in or removed from between the plates of the applicator; the non-modal interplate microwave applicator may be built into load holders that move from station to station; independent applicators for a plurality of loads may be grouped together in a compact manner to heat trays, racks, or containers very quickly; a shielding enclosure may enclose the non-modal interplate microwave applicator without acting as a modal resonant cavity, i.e. a cavity resonator.

The non-modal interplate microwave applicator may be tuned or adjusted electrically both by including an electromagnetic tuning device, e.g. an RLC circuit, and by adjusting the impedance of the plates by adjusting the distance between the plates or the area of the plates. The electrical characteristics of the applicator may also be affected by adjusting the frequency of the microwave source; the plates of the non-modal interplate microwave applicator may have various shapes, sizes and surfaces that enable loads such as tubes, tissue cassettes, flow reactors, or any object to be heated; the plates and the nonresonant enclosure may include apertures that enable temperatures such as a load temperature, or other measurable properties for example such as fluorescence, to be measured using either contact or non-contact sensors or may enable reagents to be dispensed through the enclosure and the plates.

Figure 1A:
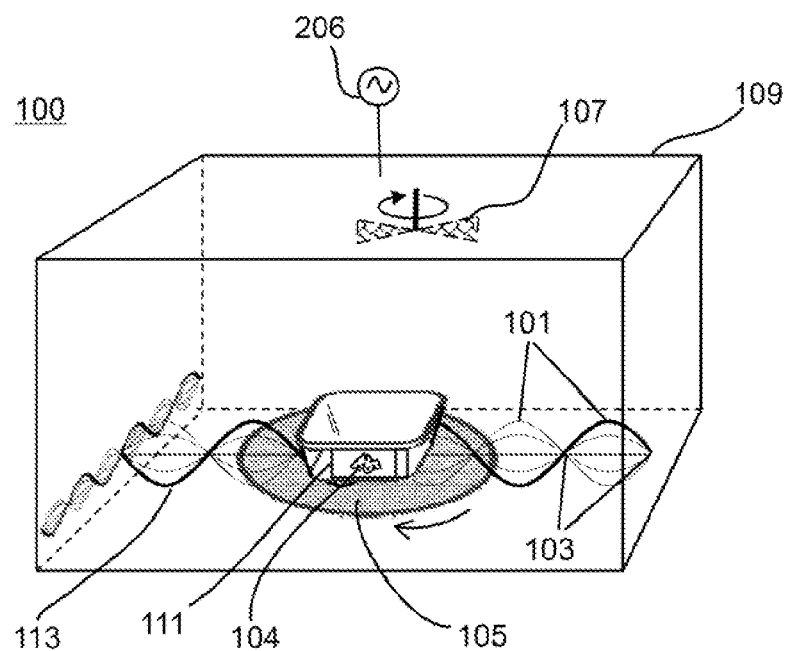
FIG. 1A is an illustration of a multimode microwave applicator system that relies on a resonant cavity.

The above beneficial effects and other advantages that non-modal interplate microwave applicators may have, compared with single-mode and multimode microwave systems, are illustrated in the drawings and discussed in greater detail below. The embodiments described herein are exemplary and one skilled in the art can readily see that many equivalent embodiments and applications may be implemented within the scope of the invention FIG. 1A illustrates a multi-mode microwave applicator 100, with a load 104 on load holder 111 e.g. a microscope slide positioned within the applicator. An applicator is a device for transferring electromagnetic energy from a source to a load. As illustrated with respect to microwave applicator 100, a microwave source 206 emits microwave energy 118 into a resonant cavity 109. Microwaves typically have wavelengths between 1 cm and 1 meter and operate in a frequency range between 300 MHz and 30 GHz. A microwave source 206 with a frequency of 2.45 GHz has a penetration depth suitable for many applications including laboratory reactions. The wavelength of microwaves at 2.45 GHz is about 12.2 cm in air. In microwave applicators that include a resonant cavity the microwave energy 118 develops a modal pattern of standing waves 113 with minima and maxima. This leads to corresponding patterns of high energy density and low energy density or hot and cold spots representing the minima (or nodes 103) and maxima (anti-nodes 101) of the multi-mode pattern in the cavity. Multi-mode microwave applicators that have a resonant cavity 109 are typically dimensioned to have a size that is typically several wave lengths in all three dimensions. The mode pattern with its regular minimum and maximum will vary depending on the position of the load and the dielectric properties of the load. This makes it very difficult to control such an applicator especially if the load 104 is small compared to the cavity dimensions and has varying dielectric properties and volume from time to time such as for reaction mixtures and tissue samples. In some multi-mode microwave applicators, devices such as a mode stirrer or field stirrer 107 may be included to change the modal pattern of the microwave radiation within the cavity in order to reduce the unevenness of the heating of the load. Further, a turntable 105 may be included to move the load 104 through the mode patterns also to reduce the unevenness of the heating of the load. Since heating may be uneven, laboratory techniques using microwave heaters often include a liquid load which is heated have a thermal and electromagnetic stabilizing effect, again to reduce the unevenness of the heating. Heat from the liquid may be transferred to the sample so that a significant portion of the microwave heating is indirect.

Figure 1B:
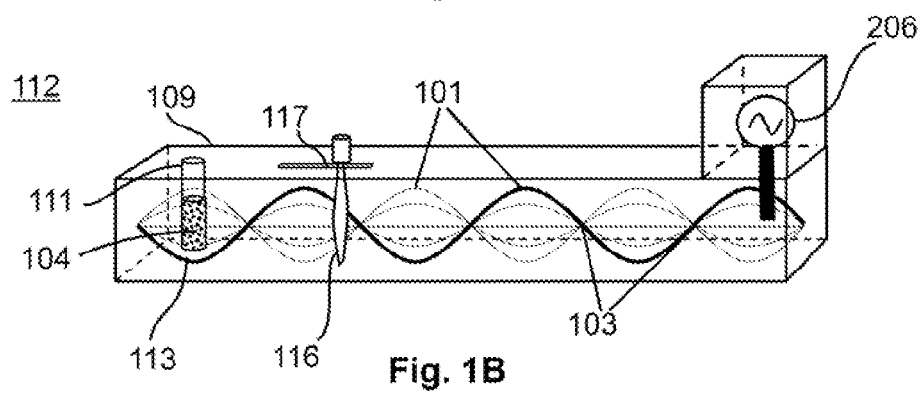
FIG. 1B is an illustration of a rectangular resonant cavity single-mode microwave applicator.

FIG. 1B illustrates a single-mode microwave applicator 112 with a microwave source 206 that generates microwave energy which forms a standing wave 113 having nodes 103 and antinodes 101. The resonant cavity 109 is dimensioned to have the desired resonance characteristics which enable the desired mode pattern. For example, a waveguide for 2.45 GHz microwaves may typically have a dimension of 43 mm×86 mm. The load holder 111 may be placed so as to position the load 104 at an antinode or maximum within the standing wave. Since the presence of a load 104 may affect the position of the minima 103 or nodes and maxima 101 or antinodes of the mode patterns, a physical tuning device 116 such as a stub of a conducting or absorbing material be positioned and moved back and forth using slot 117 within the cavity 109 to adjust the position of the minima 103 and maxima 101.

Figure 1C:
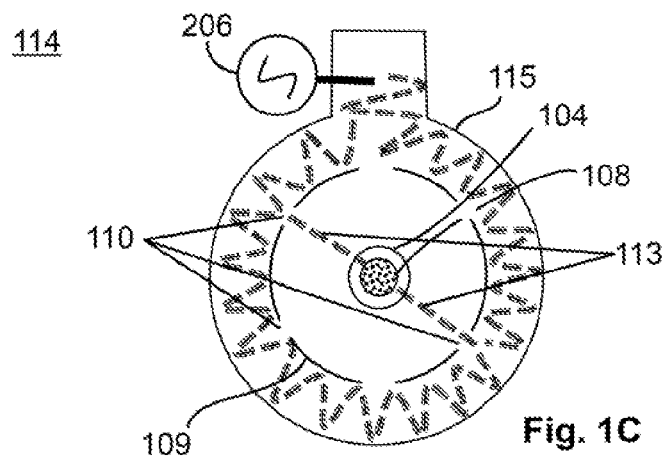
FIG. 1C is an illustration of a cylindrical resonant cavity single-mode microwave applicator.

FIG. 1C illustrates another single-mode microwave applicator 114 with a microwave source 206. A wave guide 115 is configured in a circular shape surrounding an inner cylinder 109. Inner cylinder 109 includes a series of slots 110 that act as antenna slots. The microwave energy 113 enters the inner cylinder 109 through the slots 110. Which of slots 110 the microwave energy 102 enters through may change depending upon the load 104 in the load holder 108, thus the microwave energy 111 may be focused or tuned automatically without manually adjusting a physical tuning device.

However, the single-mode microwave applicators illustrated in FIG. 1B and FIG. 1C are typically best suited for heating a single cylindrical load such as liquid in a reaction vial. As mentioned above, multi-mode microwave applicators require relatively large resonant cavities with the correct dimensions in order to function properly.

With single mode applicators, the size of the resonant cavity is smaller, but this can also be a problem because such small dimensions can make it difficult to insert or remove a load such a one or more microwave slides. Additionally it is difficult to position a load such as a microwave slide with a sample to be heated appropriately in a single-mode microwave applicator because some parts of the sample may be located at the point of maximum energy density of the standing wave while other parts of the sample may be offset slightly or significantly, thus uneven heating which could be less noticeable with a small reaction vial may be very uneven and troublesome on a tissue sample on a microwave slide.

Figure 2A:
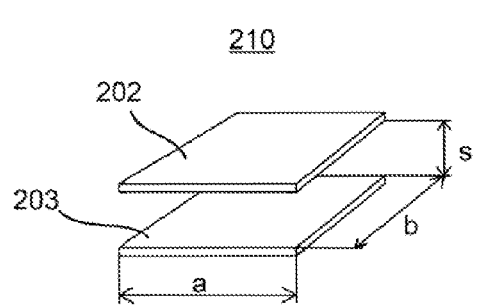
FIGS. 2A-2B are illustrations of a non-modal interplate microwave applicator embodiment of the invention.

FIG. 2A illustrates a non-modal interplate microwave applicator 210 that includes a first plate 202 and a second plate 203. The plates 202 and 203 may be of any suitable material such as metal or other conductors or they may be of semiconductors. Plate 203 is illustrated as having a width (a) and length (b). A separation distance(s) separates plate 202 and plate 203. The impedance of applicator 210 is determined, at least in part, by dimensions (a and b) of the two plates 202 and 203 and the distance(s) between the two plates. The impedance of applicator 210 should be appropriately matched to the intended load 204 in order to provide heat.

Applicator 210 surrounds the load 204 partly or completely and that the distance(s) between the plates 202 and 203 is typically less than $\lambda/6$ where $\lambda$ is the wavelength of the applied microwaves. In other embodiments the distance(s) between the plates 203, 203 may be larger than $\lambda/6$, for example it could be $\lambda/2$ in some cases. The distance(s) should be sufficiently great to avoid arcing and sufficiently small to provide an even field of microwave energy to the load.

The dielectric properties e.g. dielectric constants, of substances e.g. air or other fluid, and the load 204 between plates 202 and 203 also affect the impedance of applicator 210. The size and form of the plates 202 and 203 the distance(s) can have any value that creates the appropriate impedance of the applicator. In many embodiments, plate 202 and plate 203 both have the same or similar dimensions but there may be applications where the dimensions of 202 and 203 may differ, for example as illustrated in more detail below in the description of FIGS. 12C and 12D. Further plate 202 may in some embodiments be made of a different material than plate 203.

Figure 2B:
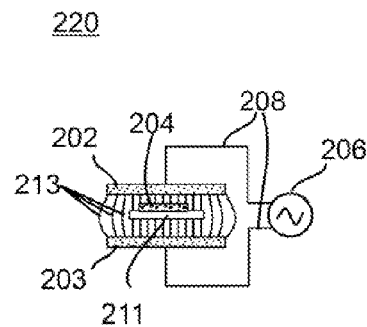

FIG. 2B illustrates a non-modal interplate microwave applicator 220 that includes plates 202 and 203 which are connected via transmission lines 208 to microwave source 206. A load holder 211 with a load 204 is positioned between plates 202 and 203. When microwave source 206 generates microwave energy, a substantial portion of the electromagnetic field, i.e. microwave energy 213 passes between plates 202, 203 through the load 204. Electromagnetic radiation, i.e. microwave energy 213 may also be transmitted away from the plates but standing waves like those in a single-mode or multi-mode microwave applicator will not build up if care is taken to ensure that any enclosure surrounding the applicator 220 does not act as resonant cavity.

In the non-modal interplate microwave applicator 220 and in the other embodiments of the invention, the RF voltage between the plates 202,203 is substantially the same everywhere because the area of the plates is small compared to the wavelength.

When two plates 202, 203 are parallel and separated by a dielectric, e.g. a gap with air, fluid, or other dielectric, there is continuity of displacement current across the boundary between the plates. Likewise, if a second dielectric, e.g. a dielectric load holder 211, partially fills the gap there will be continuity of displacement current across the boundary of the two dielectric regions. The relative values of the electric field inside and outside the load can be determined. The electric field or microwave energy 213 inside the load is the source of heating.

In this case of two dielectrics filling the gap, one being air and one being the load, continuity of displacement current means that the vector D has the same amplitude in both regions. Thus, $$D = (\varepsilon_0 \varepsilon_1' E_1) = (\varepsilon_0 \varepsilon_2' E_2)$$

and so $$E_2 = (\varepsilon_1/\varepsilon_2) E_1$$

Thus the electric field is less in the load than in the airspace by the factor of $(1/\varepsilon_2')$ Continuity of displacement current across a dielectric boundary means the component of displacement current normal to the boundary interface is at its maximum and this is used in the non-modal interplate microwave heating applicator.

Figure 2C:
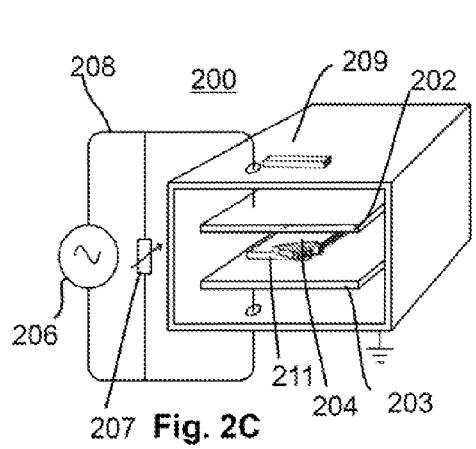
FIGS. 2C-2D are illustrations of a non-modal interplate microwave applicator embodiment of the invention with a tuning device and a nonresonant shielding enclosure.

FIG. 2C illustrates an embodiment of a microwave heating system 200 that includes a nonresonant enclosure 200 and an applicator 210 formed by two metal plates 202 and 203 surrounding a load 204 on load holder 211. The nonresonant enclosure 209 may have various dimensions and may be formed from various materials.

The applicator 210 is connected to a microwave source 206 (e.g., microwave generator) via a transmission line 208, for example, a coaxial cable. The nonresonant enclosure 209 may be configured to be nonresonant by selecting dimensions to fulfill cutoff conditions for a selected frequency.

The impedance of applicator 210 may be matched appropriately by selecting suitable dimensions or by using one or more electrical tuning devices 207 that vary the electromagnetic characteristics of the microwave energy coming from the source 206 to the plates 202, 203. For example, by tuning the Resistive/Inductive/Capacitive (RLC) characteristics of the tuning device 207, the overall impedance matching of applicator 210 can be adjusted, thereby affecting the efficiency of the heating system. Tuning device 207 as referred to herein is generally a network containing either passive or active components that attempts to match the impedance of the active device to a transmission line. By monitoring, for example, the reflected power or the temperature of the load and using that as a feedback signal to the tuning device, the applicator can be tuned to optimize the heating efficiency of the system.

It should be noted that when the term impedance or impedance matching is used herein with respect to an applicator, the term generally refers to an applicator having some degree of impedance matching between the applicator and the load. The degree of impedance matching can vary during the heating process and between different loads and run conditions. The degree of impedance matching can vary from close to zero to 100%. As long as the applicator has a degree of impedance matching, a certain amount of energy will be transferred to the load. It should be noted that impedance matching does not mean that the impedance conditions have to be maximally matched or near optimally matched during any period of the process. It is sufficient to have some degree of impedance matching in the applicator. The total energy transferred to the load will be a function of the efficiency and the amount of power applied to the applicator. Many different applications, some of which are described herein can be performed with a very low efficiency without losing microwave heating performance. Also, the field concentrating effect and uniform heating will remain even with a very low efficiency in the system.

A general, non-modal applicator made of two conducting plates will create an electromagnetic field between the plates if a microwave signal is provided between the plates. The field will have a strong electrical component between the plates largely contributing to the heating of any dialectical load placed between the plates. In practice, a general applicator of this type will more or less radiate an electromagnetic field in all directions whereby it may be desirable to have a shielding enclosure. However, if the shielding enclosure has dimensions correlating to resonant conditions at the given frequency the enclosure may act as a resonance cavity resonating above cut-off frequency and thus create a mode pattern with standing waves inside the enclosure which can disturb the function of the applicator and make the applicator less controllable. For example, as mentioned about, a waveguide for 2.45 GHz microwaves may typically have dimensions of 43 mm×86 mm. Therefore nonresonant enclosure 209 could have dimensions smaller than 43 mm×86 mm in at least one dimension. For example nonresonant enclosure 209 could be dimensioned 40 mm×40 mm or smaller, thus creation of standing waves within nonresonant enclosure 209. Larger or smaller dimensions may be used as long as care is taken to inhibit the creation of standing waves that could affect the field between plates 202 and 203.

By keeping the dimensions of the enclosure less than dimensions correlating to resonant conditions i.e. below cut-off frequency, this disturbance can effectively be avoided. Another way to achieve a nonresonant enclosure is to include an absorbing or attenuating material in the enclosure. This is one way that a shielding enclosure could be used while still having dimensions greater than for cut-off conditions.

As used herein, nonresonant enclosure refers to an enclosure that encloses or at least partially encloses a microwave applicator without creating significant mode patterns or standing waves, and without relying on the enclosure to focus otherwise concentrate the microwave energy in order to heat.

The nonresonant enclosure 209 may include an electrically conducting surface and in the illustrated embodiment is rectangular in profile. For example, the nonresonant enclosure 209 may form an electrically conducting cavity constructed from aluminum, copper, brass, semiconducting material or a combination of materials, etc. However, it should be noted that other materials may be used.

The various embodiments of the invention do not rely upon the nonresonant enclosure to build up maxima or hot spots through standing waves or to otherwise reflect, focus or concentrate the microwave energy in order to create a concentrate field of microwave energy. However, the nonresonant enclosure 209 may serve as an electromagnetic shield to inhibit or prevent microwave radiation from escaping or otherwise generating electromagnetic interference that might affect items outside the nonresonant enclosure. Accordingly, the material of the nonresonant enclosure may have apertures or holes or may be made of mesh which acts as an electromagnetic shield.

Also, it should be noted that the nonresonant enclosure 209 may have a different shaped profile other than rectangular, for example, spherical, elliptical, cubic, triangular, cylindrical etc. The nonresonant enclosure 209 may be shaped and sized based on and configured to receive therein a complementary shaped load holder 211, for example, a microscope slide or a reaction vial, which may be removable therein or permanently secured therein. Although various embodiments of the microwave applicator 200 are very suitable for heating planar loads such as microscope slides and tissue cassette, it should be noted that the various embodiments also are not limited to a reaction vial or a glass slab, but a container or structure may be provided that is of any type that can receive therein or on its surface a fluid or other object. For example, instead of a reaction vial, a bulb, tube, a capillary structure, a thin film substrate, glass slab, microscope slide, micro titer plate, micro fluidic devices, micro arrays, micro fabricated structures, etc. may be provided.

Moreover, the cutoff frequency for the nonresonant enclosure 209 in one embodiment is determined by the dimensions (h), (w), and (d) of the nonresonant enclosure 209. Accordingly, the dimensions in many embodiments are selected to be small enough to prevent the modal propagation of certain microwaves, for example, 2.45 GHz microwaves.

In the various embodiments, the applicator 210 is configured to substantially surround the load 204. Accordingly, in operation, a very broadband frequency and a homogenous electric field that couples and interacts with the load 204 in many places is provided. It should be noted that the applicator can have any dimensions as long as the impedance of the applicator and the load are sufficiently matched to provide the desired heating effect.

The applicator 210 in various embodiments is formed from metal plates dimensioned to sustain the required output power. The output power may be very low in comparison with the output power required by single-mode or multi-mode resonant cavity microwave applicators. For example, the output power might be from 1 milliwatts to 100 milliwatts, 100 milliwatts to 1 watt, 1 watt to 10 watts, or 10 watts to 100 watts or more depending on the size and configuration of the plates, the load to be heated, and the characteristics of the microwave source.

In some embodiments, the applicator 210 may be formed from one millimeter (1 mm) thick plates 202, 203, such as copper, gold, brass, aluminum, metal coated structures with a core of non-conducting materials such as polymers, semiconducting materials or combination of mentioned materials. In some embodiments, the plates 202, 203 may be thick enough to sustain an electric field generated by, for example, 100 watts to 500 watts of power or more. The applicator 210 may also be formed from a printed circuit board arranged around the load. The printed circuit board can be of a flexible type that can be formed around the load. The applicator can also be stereo lithographically printed on a substrate and arranged around the load.

In operation, the load 204 is placed or secured inside or partially inside the applicator 210. A homogeneous electric field will be established between the two applicator plates and accordingly the load will be exposed very evenly to the electromagnetic field and thereby generating a very uniform heating of the load. For many typical embodiments, electric field propagated from the applicator 210 is also contained within the conductive enclosure, namely the nonresonant enclosure 209. However, since very low power may be used in the various embodiments, a very low degree of shielding or in fact no shielding may be required.

It should be noted that the various embodiments can be operated using a multiple microwave source 206 and applicator 210, which in the various embodiments is either a single ended applicator or a balanced applicator. The applicator 210 can be made to have broadband to narrowband characteristics with corresponding low Q to high Q values. Accordingly, the applicator 210 can have a sufficiently matched impedance with the load over a wide band of frequencies. The frequency band characteristics can be chosen depending on the application. Often a broadband characteristic is desired where the applicator is not highly matched to a particular frequency. Thus, the configuration of the microwave heating system 200 is less dependent on the load 204 to be heated.

Figure 2E:
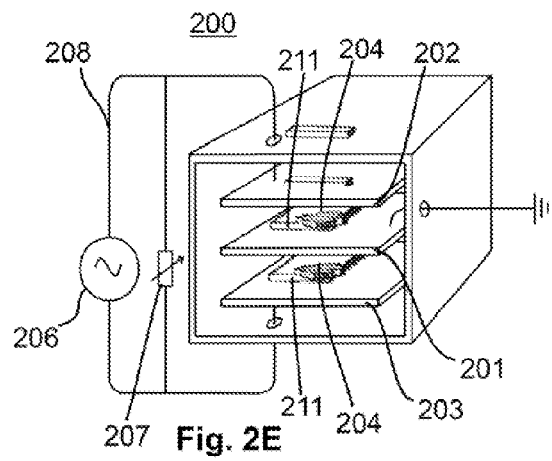
FIG. 2E is an illustration of a non-modal interplate microwave applicator embodiment of the invention with an added center plate that connects to ground.
Figure 2D:
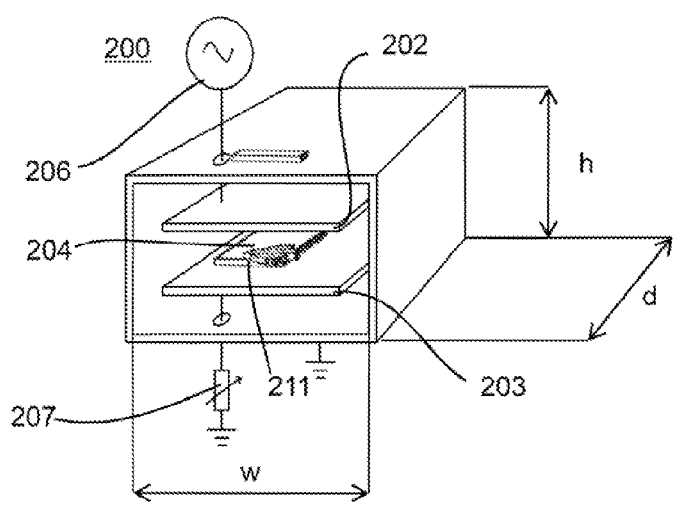

In various embodiments, the applicator type can be either be a balanced applicator as shown in FIG. 2C, or a single-ended closed-loop applicator where one end can be connected to earth, as shown in FIG. 2D. The balanced applicator can be fed symmetrically using a balance-to-unbalance transformer (balun). A balun as used herein refers to a device that converts a single-ended transmission line to a symmetrical pair of transmission lines having exactly the same properties and symmetrical to ground. A single ended applicator is a device as used herein refers to an applicator fed by a single transmission line and usually fed at one end. A balance applicator as used herein refers to an applicator that is fed by two symmetrical transmission lines with respect to ground. It should be noted that in all described embodiments, all described types of applicator can be used even if only one type is described in a specific embodiment.

The characteristics of the applicator and thereby the generated electrical field can be adjusted or customized to surround the load by combining certain values of the applicator parameters such as the area of the applicator plates, the plate dimensions (a) and (b), and the separation distance(s) between the applicator plates, and the physical form of the plates. By changing these parameters the electrical field can, for example, be evenly distributed over the load. The electric field strength and distribution is also affected by any dielectric material introduced between the applicator plates. The load holder and other holding structures and components will contribute to the electric field distribution in the applicator. However, any enclosure such as nonresonant enclosure 209 should dimensioned or otherwise configured so as to avoid causing standing waves to build up as occurs with single-mode and multi-mode microwave applicators.

Referring again to FIG. 2A, the plate dimensions (a) and (b), the separation distance(s) between the applicator plates and the physical form of the applicator 210 determines an impedance and center frequency for the applicator 210. Accordingly, depending upon the application or use for the microwave heating system 200, the plate dimensions (a) and (b), the separation distance(s), between the applicator plates and the physical form of the plates may be adjusted accordingly, for example, to provide desirable, required or optimum dimensions. The shape of the plates can have any geometric shape such as elliptic, circular, square, rectangular, triangular, octahedral, polyhedral, or any other single or double curved surfaces.

In the various embodiments, the applicator 210 is a single ended applicator or a balanced applicator that covers part of or the entire load 204. However, it should be noted that the load 204 in some embodiments may extend beyond the ends of the applicator 210.

FIG. 2E illustrates an embodiment of a non-modal interplate microwave applicator 200 that may be substantially similar to the balanced embodiment illustrated in FIG. 2C with an added center plate 201 that connects to ground. The added center plate enables two loads 204 and two load holders 211 to be positioned between the plates such that a balanced non-modal interplate microwave applicator is formed and the load capacity is doubled. Other embodiments of a three-plate or even "n"-plate non-modal microwave applicators can be constructed using planar plates, undulated plates, cylindrical plates or any type of plates by connecting a microwave source to one plate and a ground to the adjacent plate and repeating this structure "n" times.

Figure 3A:
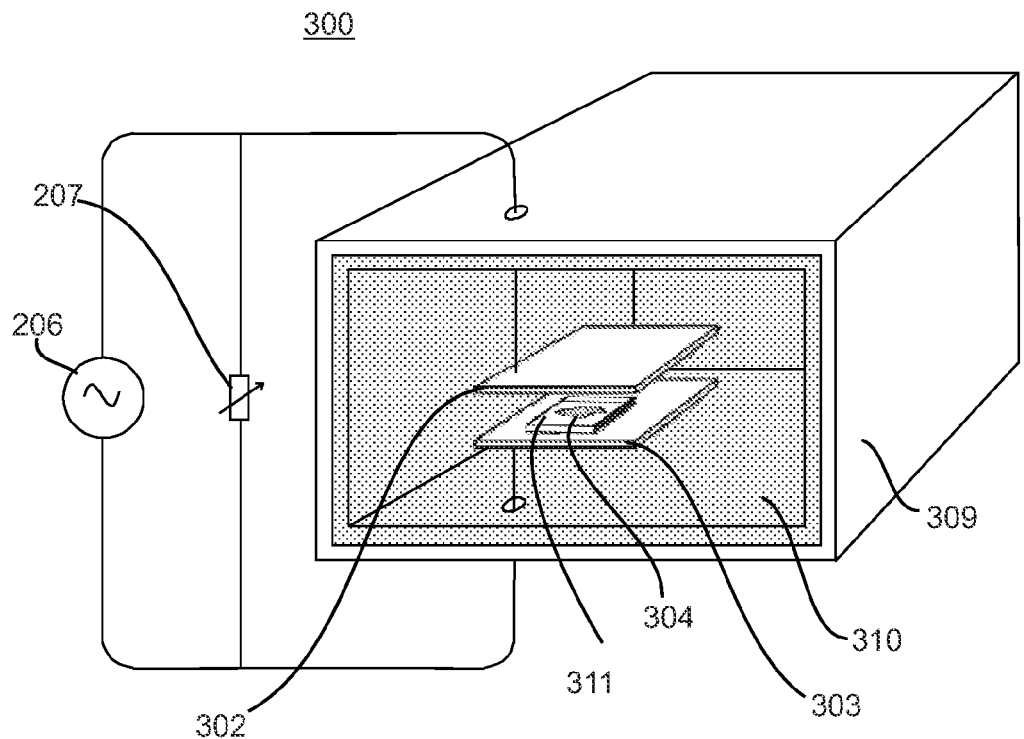
FIGS. 3A-3B are illustrations of a non-modal interplate microwave applicator with a nonresonant enclosure having a microwave attenuating inner surface.

FIG. 3A illustrates a non-modal interplate microwave applicator 300 with a nonresonant enclosure having a microwave attenuating inner surface 310. Depending on the power being applied, the microwave attenuating inner surface 310 may be beneficial in some embodiment to prevent build up of mode patterns, standing wave, or other interfering signals that might interfere with the desired operation of the applicator 300. In embodiments where the power is low, the need for a specifically microwave attenuating surface may be diminished. The microwave applicator 300 has a microwave source 206 that is connected in a balanced configuration to a tuning device 207 and to plates 302 and 303. A load 304 is positioned on a load holder 311 between plates 302 and 303. Enclosure 309 may have dimensions that prevent build of modal microwave energy, i.e. small than the wavelength of the desired cutoff frequency. However, other dimensions may also be used for the enclosure 309 while maintaining substantial nonresonance. A surface 310 that is substantially non-reflective to the desired microwave frequency may be included. The surface 310 may be formed of microwave attenuating material or may be coated with a microwave attenuating coating. Examples of microwave attenuating material may include many types of absorbing or scattering materials such as conductive foam or microwave absorbing paint that includes thin conducting fibers such as stainless steel fibers or carbon or graphite mixed paint or other coating material.

Figure 3B:
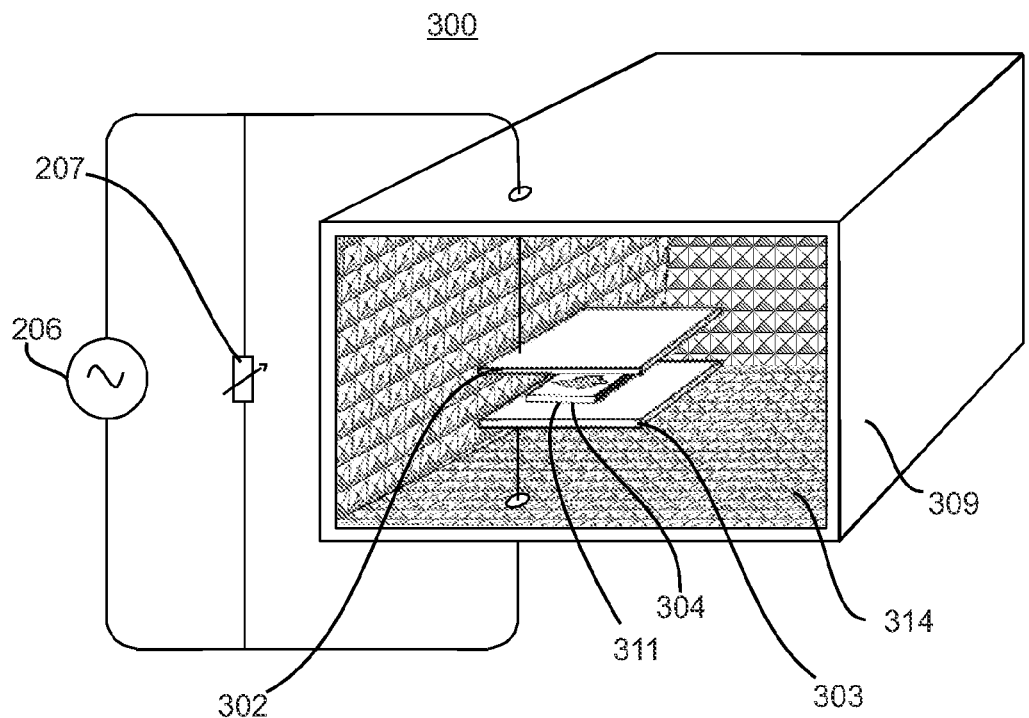

FIG. 3B shows that a microwave attenuating surface 314 may be included in enclosure 309 to create a nonresonant enclosure. The microwave attenuating surface 314 may include elements used in anechoic chambers such as cones, baffles, pyramids, or other protruding physical structures designed to trap and attenuate microwaves.

To illustrate certain advantages of non-modal interplate microwave applicator such as those described in FIGS. 2A-2D and FIGS. 3A-3B, consider that conventional multimode microwave applicators that rely on the creation of standing waves or modal patterns include resonant cavities would in general be too bulky for integration in to multiple stations within a single instrument. Those types of applicators have been described above with reference to FIG. 1A-1C. Further, those types of applicators are not well adapted to handle multiple flat specimens on microscope slides. However, non-modal interplate microwave applicators such as those describe in the various embodiments of the invention may be very well suited for multiple instantiations within a single instrument especially where the loads are small planar loads such as microwave slides and also for inline heating of tubing which may carry rinse or other fluids or reagents to the microscope slides.

Figure 4:
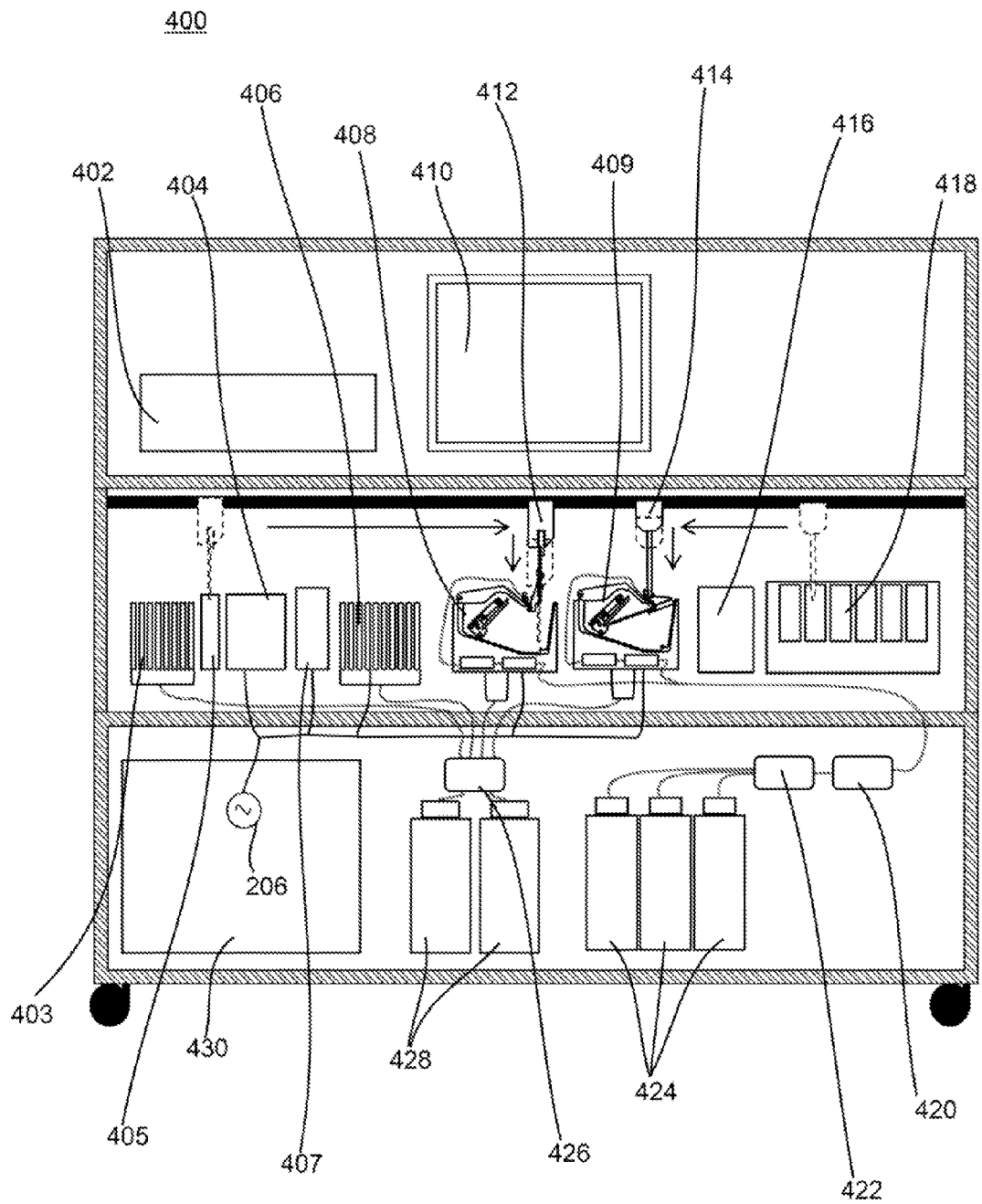
FIG. 4 is an illustration of an automated slide staining system including stations that may be configured to include various embodiments of a non-modal interplate microwave applicator.

FIG. 4 is a diagram of an automated slide staining system 400 which serves as one example of how various embodiments of the non-modal interplate microwave applicator may be adapted for multiple uses within an instrument. Because the various embodiments of non-modal interplate microwave applicators can be made to be compact, and to use relatively low power in comparison to microwave applications with resonant cavities, such embodiments may be very beneficial to be used in instruments or systems such as the automated slide staining system 400. Further automated slide staining system 400 is configured to process multiple samples in parallel which processing requires controlled heating various points in the staining process. Additionally, interplate microwave applicators as described herein have the benefit of being very well suited to heat where multiple independent controllable heaters are required. Also, non-modal interplate microwave applicators may be configured to heat flat loads such as cells or tissues on microscope slides, tissue cassettes or any load that fits between the plates such as tubing or trays.

The automated slide staining system 400 includes a user interface 410 which may include an embedded PC and display screen. The automated slide staining system may include slide handling apparatuses such as a cover slipper 402 and a slide rack transport robot 412 that conveys slide racks with microscope slides to be stained from a slide rack port 405 to various processing stations. Processing stations may include: a waiting station 403 where slides in slide racks are held prior to, during or after other processing steps; a baking station 404 where tissue samples are baked to ensure adhesion of the sample to the slide; a dewaxing station 406 where paraffin is removed from the samples on the slides; a target retrieval station 407 where heat induced epitope retrieval is performed; an immunohistochemistry (IHC) staining module 408; a in-situ hybridization (ISH) staining module 409. Staining system 400 may include a robot probe 414 that moves between reagent mixing and probe wash station 416, reagent station 418, and staining modules 412 (IHC) and 414 (ISH). Bulk fluid bottles 424 may contain fluids for rinsing, buffering, and may be connected to valves 422 and pump 420 to deliver fluids to target retrieval station 407, dewax station 406, IHC staining module 408, and ISH staining module 409. Waste fluids from stations and modules may be connected to waste containers 428 through fluid management module 426. A control module 430 may include a microwave source 206 which connects to the modules requiring a microwave source.

Figures 5A, 5B:
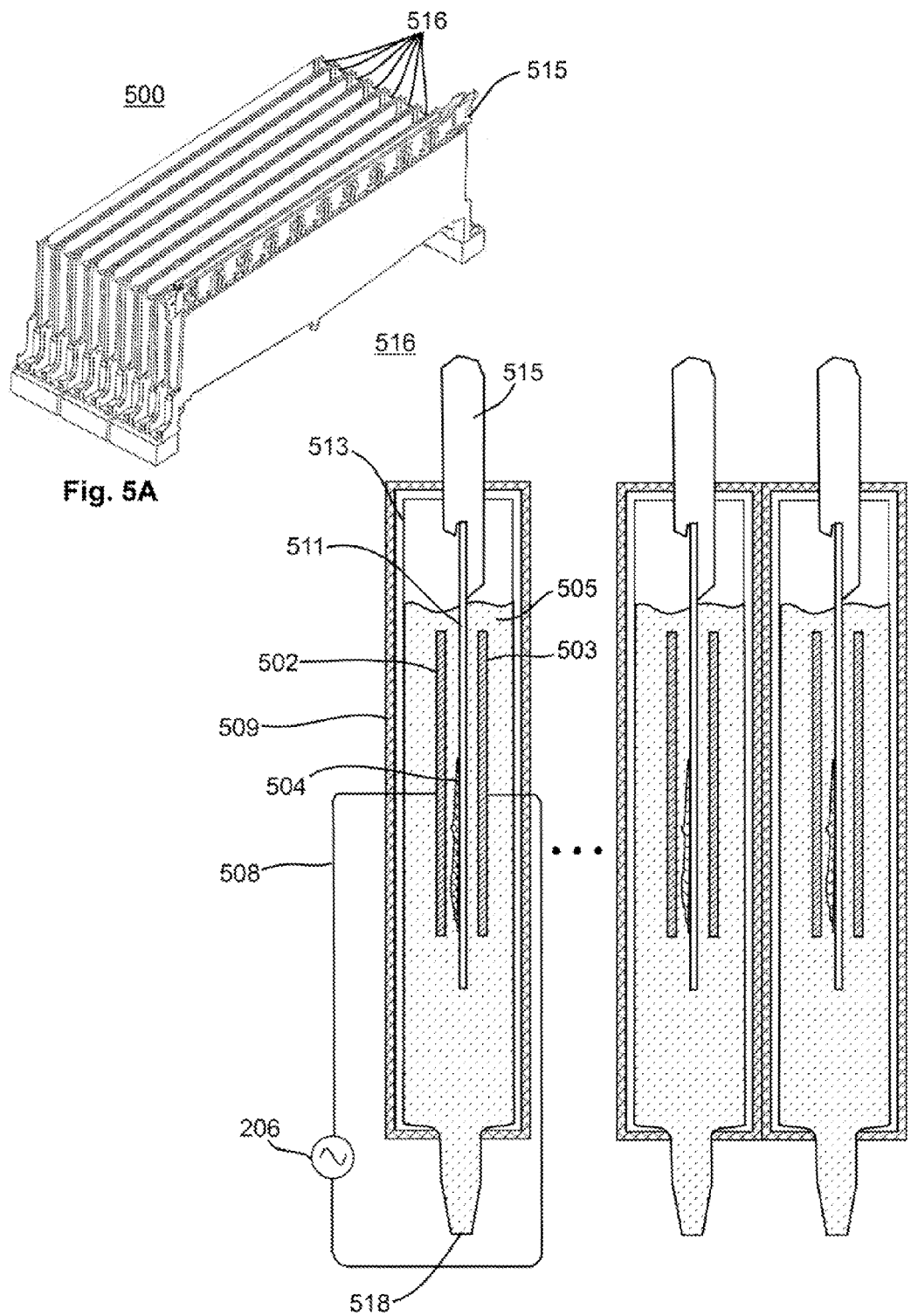
FIGS. 5A-5B are illustrations of diptanks with immersed non-modal interplate microwave applicators and nonresonant enclosures.

FIG. 5A is an orthogonal view of a diptank module 500 with individual diptanks 516. A slide rack 515 may be inserted into one of the diptanks 516. A very clear advantage of using an embodiment of the invention, i.e. the non-modal interplate microwave applicator, in such an application is that multiple diptanks 516 each having an independent non-modal interplate microwave applicator can be placed together in close proximity. It would be very difficult to achieve closely joined but independent microwave diptank applicators using either single mode or multi mode microwave applicators which require resonant cavities.

FIG. 5B illustrates an end view of a diptank 516 with a non-modal interplate microwave applicator. Plates 502 and 503 are connected via transmission line 508 to a microwave source 206. The load 504 may be a tissue sample that is to be deparaffinized via heating in a liquid 505. In this embodiment, the plates 502, 503 may be immersed in a paraffin-removing liquid 505 contained in a liner or container 513. Container 513 may be made of any material that does not act as a resonant cavity. It may further be made of material that either conducts or transfers heat well or alternatively a material that insulates well depending on whether the particular application requires heat to be retained or dissipated. In some applications it may be advantageous to coat plates 502, 503 and transmission line 508 so that it is not directly exposed to liquid 505. Such coating of course may be designed to be substantially transparent to microwaves. A slide rack 515 holding one of more slides/load holders 511 may be introduced into the diptank 516 and fluid may enter or leave the diptank through a port 518 at the bottom of diptank 516. A nonresonant enclosure 509 surrounds a liquid container 513 and may act to shield adjacent diptanks 516 and their contents from microwave radiation emitted from plates 502 and 503. The nonresonant enclosure 509 may be dimensioned to be small enough to prevent standing waves from developing. Alternatively nonresonant enclosure 509 may be made nonresonant using materials or coatings that attenuate or prevent build up of standing waves. Although the plates 502, 503 are depicted as both being positioned with the liquid 503 and the container 510, other embodiments in which the plates 502, 503 are external to container 510 may be constructed.

Figure 6:
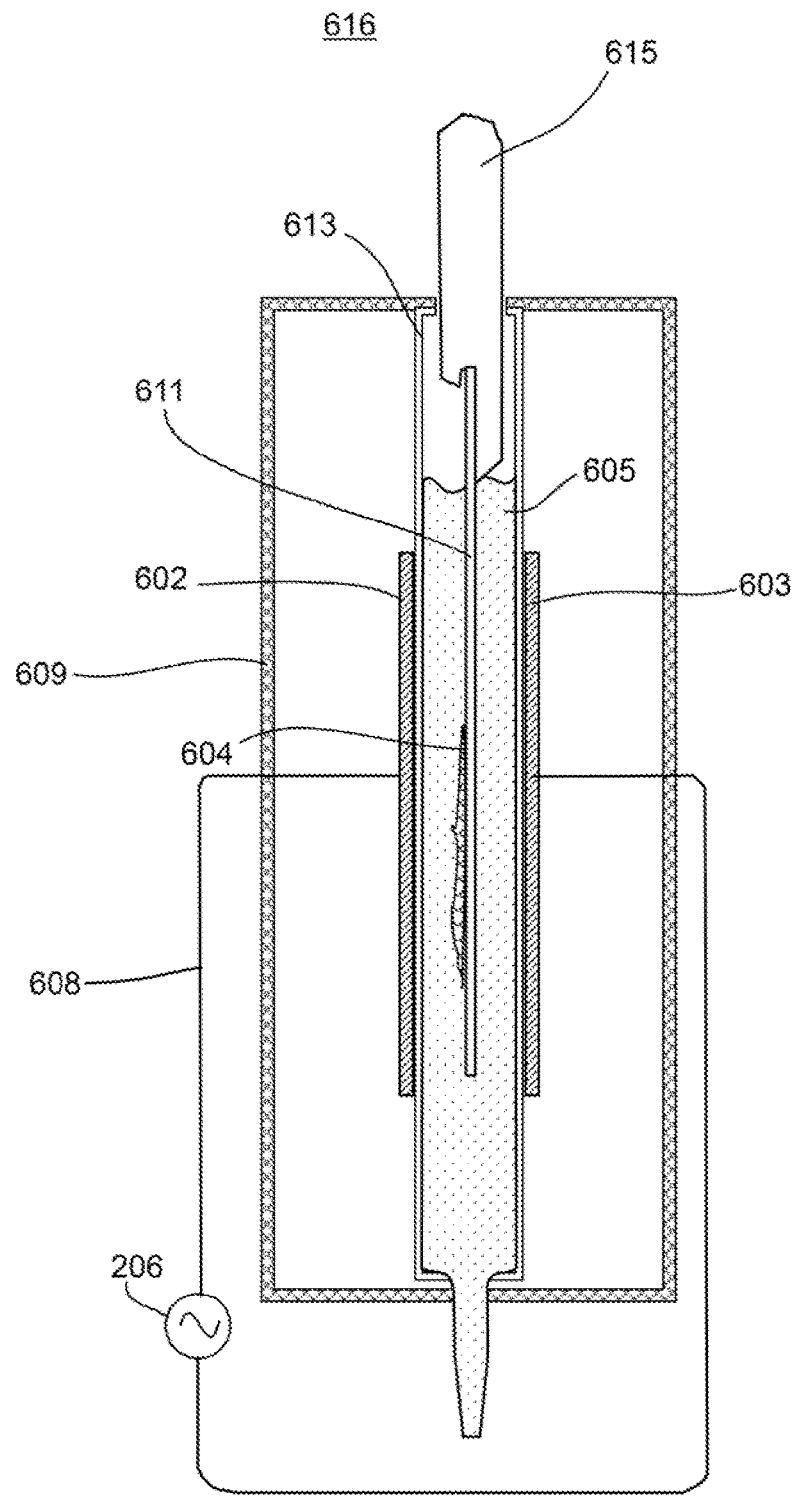
FIG. 6 is an illustration of a diptank with a non-immersed non-modal interplate microwave applicators and nonresonant enclosures.

FIG. 6 illustrates a diptank 616 with a non-modal interplate microwave applicator that is similar to the embodiment illustrated in FIG. 5A and described above. In some applications there may be a benefit to positioning the plates 602, 603 so they do not contact liquid 605 directly and do not require any special coating. In the embodiment of FIG. 6 the non-modal interplate microwave applicator comprises plates 602, 603 which are position outside liner or container 613. Plates 602, 603 connect via transmission line 608 to microwave source 206. A slide rack 615 having a slide 611 that includes a tissue sample or load 604 may be positioned within the non-modal microwave applicator plates 602, 603 and heated directly, quickly, precisely through the walls of container 613 and through the liquid 605. Nonresonant enclosure 609 acts as an electromagnetic shield but not as a cavity resonator by either being dimensioned so as to prevent mode patterns from building or by attenuating the microwaves.

Figures 7A, 7B:
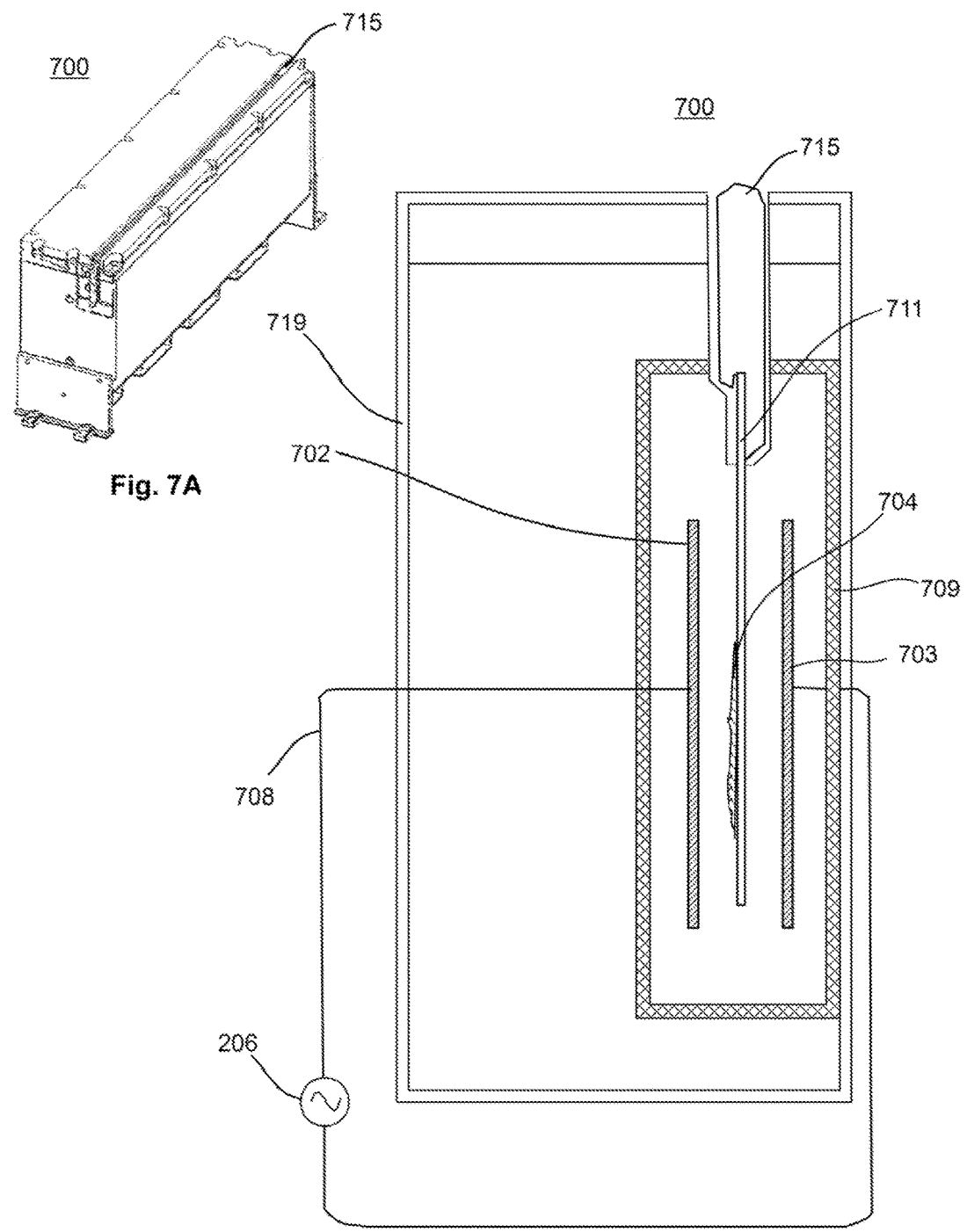
FIGS. 7A-7B are illustrations of a slide baking station with non-modal interplate microwave applicators.

FIG. 7 illustrates a non-modal interplate microwave applicator being used in a drying or baking module 700. A slide rack 715 with a slide 711 and tissue sample or load 704 may be positioned between plates 702,703 which connect via transmission lines 708 to microwave source 206. Nonresonant enclosure 709 acts as an electromagnetic shield around the plates and load. If the baking module 700 were to utilize forced hot air from conventional applicators to bake slide 711, a fairly large enclosure such as enclosure 719 may be used to enable greater airflow and convection. However a non-modal interplate microwave applicator can perform baking without depending on airflow and the accompanying large enclosure size. This also illustrates the concept that some embodiments of non-modal interplate microwave applicators may be utilized to retrofit or replace conventional applicators because they can be constructed to be relatively small.

Figures 8A, 8B:
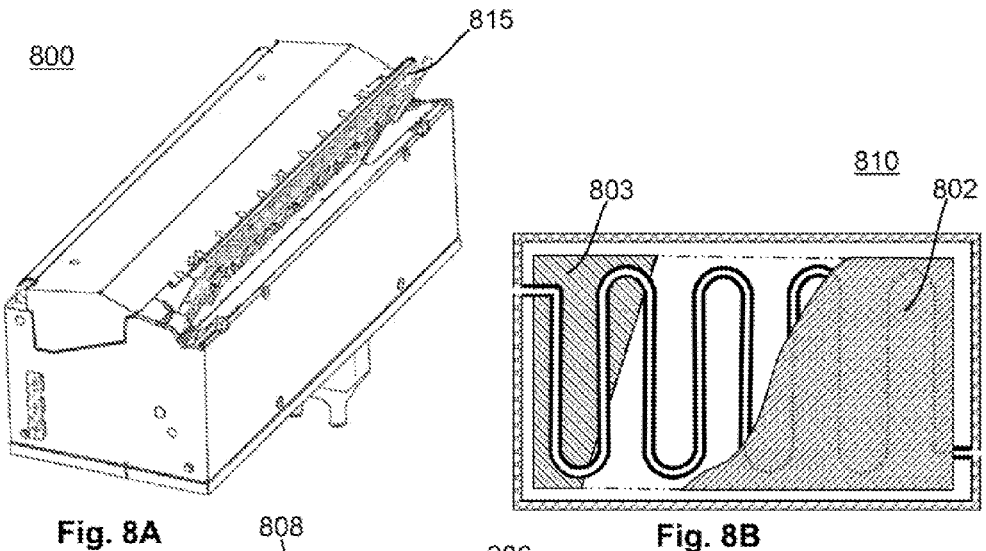
FIGS. 8A-8C are illustrations of a slide staining module with non-modal interplate microwave applicators for inline fluid heating and two-piece accessible non-modal interplate microwave applicators for direct slide sample heating.

FIG. 8A illustrates a capillary staining module 800 which can be either an immunohistochemistry staining module 408 or an in-situ hybridization staining module 409 as illustrated in FIG. 4 and the accompanying description above. As with the other exemplary modules described above, a slide rack 815 may be introduced into capillary staining module 800 for processing. With some very fast protocols, it is advantageous to heat a rinse buffer 826 that is dispensed onto slide or load holder 814 that is held by slide rack 815. By so doing the temperature of the load holder 814 and the load 824 can be maintained at a temperature nearer a desired incubation temperature rather than being cooled by applying a cold rinse. Heating the rinse buffer 826 may be accomplished by passing it through a tube 804 which when full of fluid 826 acts as a load to non-modal interplate microwave applicator 810.

FIG. 8B shows non-modal interplate microwave applicator 810 which comprises plates 802 and 803 with the load 804, i.e. fluid filled tube bending through between plates 802 and 803.

Figure 8C:
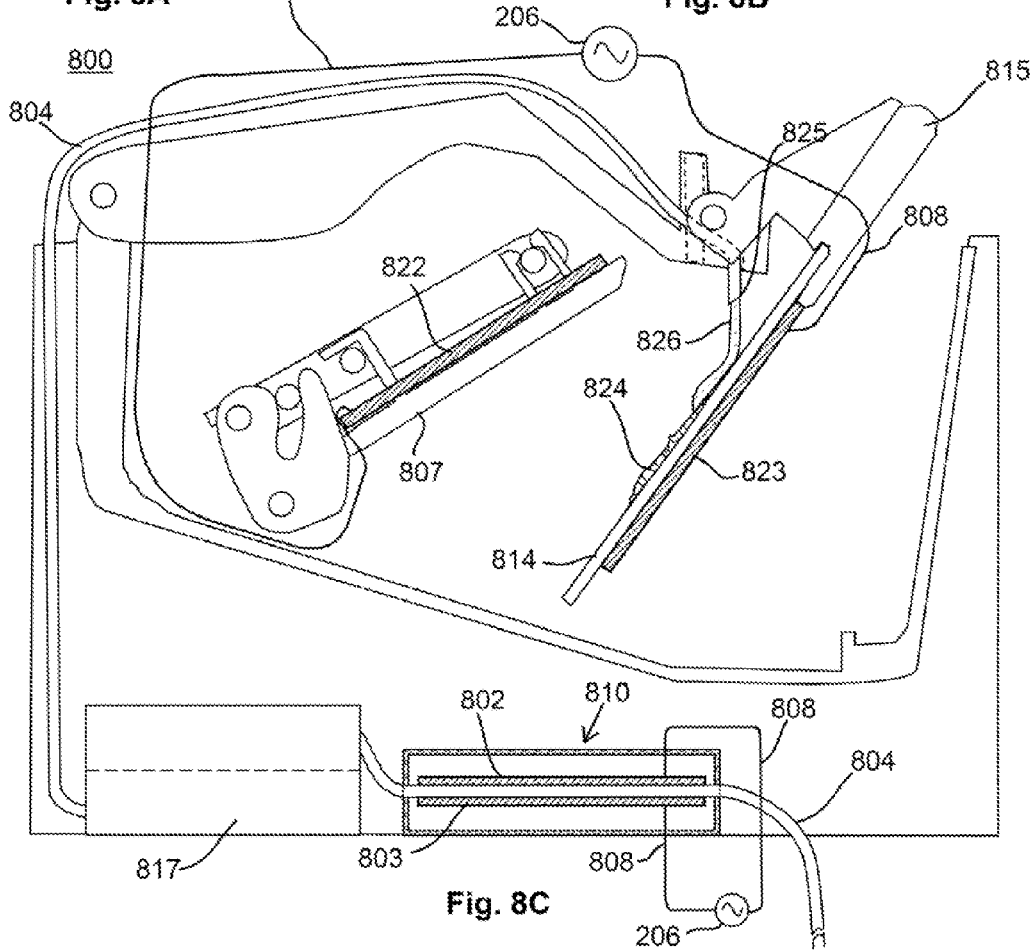

FIG. 8C illustrates a staining module 800 which is configures to pivot a slide rack 815 which holds a load holder 814 e.g. A microscope slide, so that it can be positioned to near and substantially parallel to a cover or lid 807 so that a capillary gap is formed between the lid 807 and the slide 814 when they are brought together. A fluid 826 such as a buffer may be dispensed from a dispensing nozzle 825 onto the load holder 814 and the load 824, e.g. a tissue sample that is to be stained or otherwise processed. The fluid to be dispensed may be heated using non-modal interplate microwave applicator 810 wherein a load 804, i.e. a fluid filled tube passes through plates 802 and 803 which heat the load 804 when microwave energy is applied through transmission line 808 from microwave source 206. The liquid 804 continues through a bubble trap and dispenser system 817 up to the nozzle 825.

A reagent may be dispensed through opening 825 onto slide 814. For example an antibody or a molecular probe may be dispensed so that it contacts the load 824, i.e. sample.

Also illustrated in FIG. 8C is a plate 822 positioned next to the lid 807 and a second plate 823 positioned next to load holder 814. When load holder, i.e. slide 814 and lid 807 are brought together to form a capillary gap, plates 822 and 823 which are connected via transmission line 808 to microwave source 206.

Both the inline fluid heating and the microscope slide incubation heating are exemplary embodiments that illustrate the diverse applicability of the non-modal interplate microwave applicator.

FIG. 9A and FIG. 9B depict a target retrieval module 900 with a slide rack 915 that may be inserted into module 900. The load holder or slide 911 with a load or tissue sample 904 may be positioned between plates 902, 903, which connect to microwave source 206 through transmission line 908 and are surrounded by nonresonant enclosure 909. In this embodiment, individual non-modal interplate microwave applicators with plates 902, 903 may compass separate diptanks 913 so that the fluid 905 in each diptank may be the same type of fluid or a different type of fluid and the heating temperature of the fluid may be controlled independently for each sample. In an immunohistochemistry application where different target retrieval solutions and different heating conditions may be advantageous for each slide, such an embodiment may be well-suited.

FIG. 10 illustrates a robot probe 1000 with a pipette tip 1017 which is fluid connection with a length of tubing 1011 wound about a cylinder which includes an inner cylinder plate 1003. An outer cylinder plate 1002 at least partially surrounds the wound tubing 1011 to form a non-modal interplate microwave applicator that may be used to heat the load 1004 i.e. the wound portion of the tubing 1011. The plates 1002 and 1003 of the non-modal interplate microwave applicator connect via transmission line 1008 to microwave source 206 and are enclosed by nonresonant enclosure 1009. Such an embodiment illustrates how a non-modal interplate microwave applicator may heat a fluidic load in an inline manner and thus enable heating of a fluid to be dispensed by a robotic probe while maintaining a compact robot fluidics design.

Figure 11A:
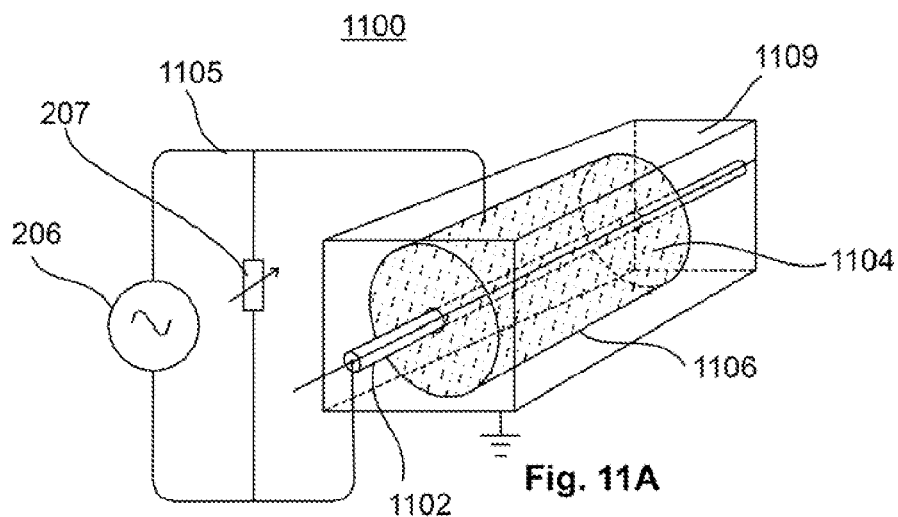
FIGS. 11A-11C are illustrations of another cylindrical non-modal interplate microwave applicator.
Figure 11B:
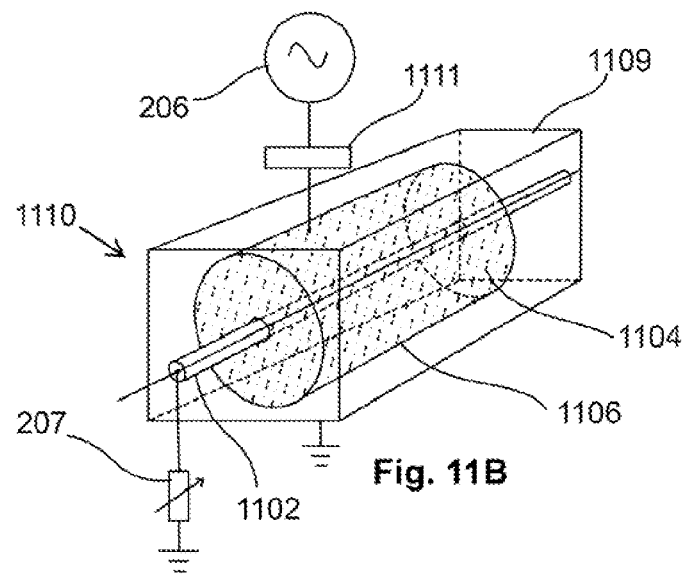
Figure 11C:
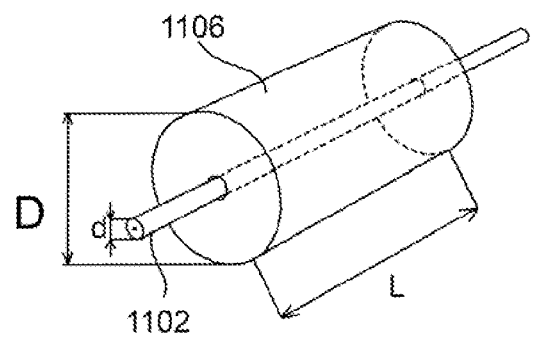

FIG. 11A shows a cylindrical non-modal interplate microwave applicator 1100 using the same principle of a non-modal interplate microwave applicator as used in FIG. 2 with a cylindrical applicator 1110 corresponding to planer plate applicator 210. The cylindrical applicator plate analogous to applicator plate 202 in FIG. 2 is formed in the embodiment of FIG. 11 as an outer cylinder 1106 and an applicator plate analogous to applicator plate 203 in FIG. 2 formed in the embodiment of FIG. 11 as an inner cylinder 1102. The load 1104 to be treated is placed between the outer cylinder 1106 and the inner cylinder 1102. The outer cylinder 1106 and the inner cylinder 1102 form together the non-modal interplate applicator in the microwave heating system 1100. The cylinders 1102 and 1106 connect to microwave source 206 through transmission line 1105 and may include a tuning device 207. The non-modal interplate microwave applicator may be a balanced configuration as shown in FIG. 11A or a singled-ended configuration as shown in FIG. 11B. Cylindrical plates 1102, 1106 can be made of a conducting or semiconducting material. The cylindrical form of 1102 and 1106 is just an example of a possible geometric form. 1102 and 1106 can have any form as long as the load can be, at least partially placed between the applicator plates. The system 1100 may also include a nonresonant enclosure 1109 that may act as a shield to prevent the propagation of microwaves at the applied frequency outside the system and create appropriate boundary conditions inside the enclosure 1107. The characteristics of the heating system will be governed by the dimensions d, D and L as defined in FIG. 11C.

A balanced applicator that is fed from an unbalanced source may be connected via a balance-to-unbalance transformer (balun). A balanced applicator is constructed symmetrically with respect to the feed point and preserves symmetry with respect to ground thus avoiding unbalanced currents and unwanted radiation in the transmission feed line. This ensures all energy is radiated more efficiently from the applicator. The balun 1111 can be physically placed anywhere between the microwave source 206 and the beginning of the applicator 1110. The balanced applicator parts and 1102, 1106 can have the same design, dimensions and features as the herein described single ended applicators parts.

Figure 12A:
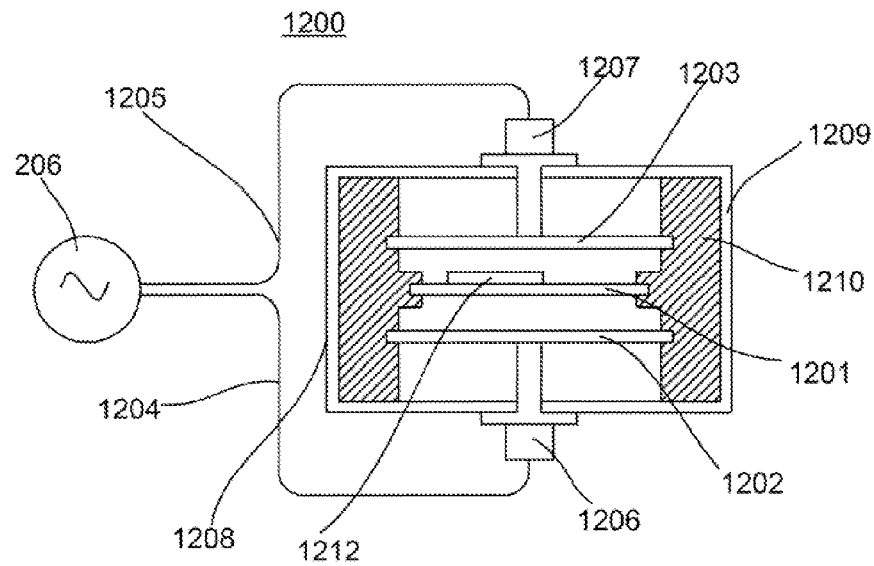
FIGS. 12A-12I are illustrations of various embodiments of non-modal interplate microwave applicator and several embodiments of plates for a non-modal interplate microwave applicator.
Figure 12B:
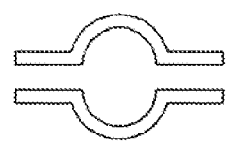
Figure 12C:
Figure 12D:
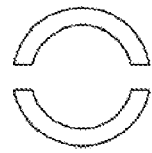
Figure 12E:
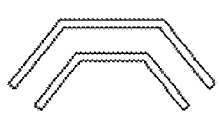
Figure 12F:
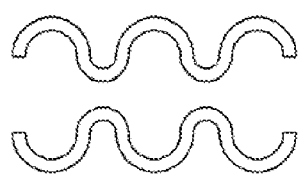

FIG. 12A illustrates a non-modal interplate microwave applicator that includes a supporting structure 1210. The supporting structure 1210 supports and maintains the position of the load holder 1201 and the load 1212 within the system 1200. The supporting structure 1210 may be formed of any suitable microwave transparent or microwave semi-transparent material, for example, a polytetrafluoroethylene (PTFE) material, such as Teflon. Also, the microwave heating system 1200 can be made nonresonant by configuring the dimensions of the enclosure 1209 to achieve frequency cutoff conditions as described herein. Similar to the descriptions of other embodiments, plates 1202, 1203 connect via connectors 1206, 1207 to transmission lines 1204, 1205 to microwave source 206. Various shapes or forms of plates may be used in the various embodiments of the non-modal interplate microwave applicator. Some examples of plate shapes are shown in FIGS. 12B-12F. FIG. 12B shows tube clamping type plates with flat tabs. FIG. 12C illustrates angled plates which may form a wedge. FIG. 12D illustrates plates that form a ring. FIG. 12E shows that plates may have multiple bends or angles as does FIG. 12F. Various embodiments of the non-modal interplate microwave applicator may be formed to any shape that allows a load to be positioned between the plates and microwave energy to be applied as desired to the load. As mentioned above with respect to FIG. 2., the distance between the plates does not need to be uniform as illustrated in FIGS. 12B, 12C, 12D, and 12F.

Figure 12G:
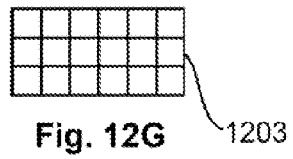
Figure 12H:
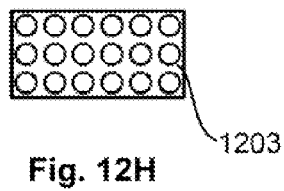
Figure 12I:
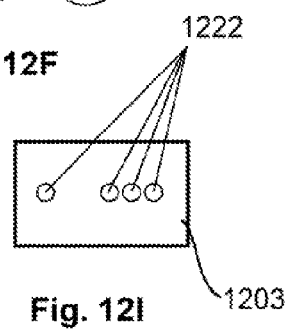

FIGS. 12G-12I illustrate the principle that the plates may also include discontinuities or apertures. For example, FIG. 12G illustrates that a plate 1203 may comprise a rectangular wire mesh. FIG. 12H illustrates a plate 1203 that includes a regular pattern of holes or apertures. FIG. 12I illustrates a plate 1203 that includes an irregular pattern or apertures 1222 which may be a single aperture or a plurality of apertures. A similar variety of plate shapes and apertures may be included in other of the embodiments.

Figure 13:
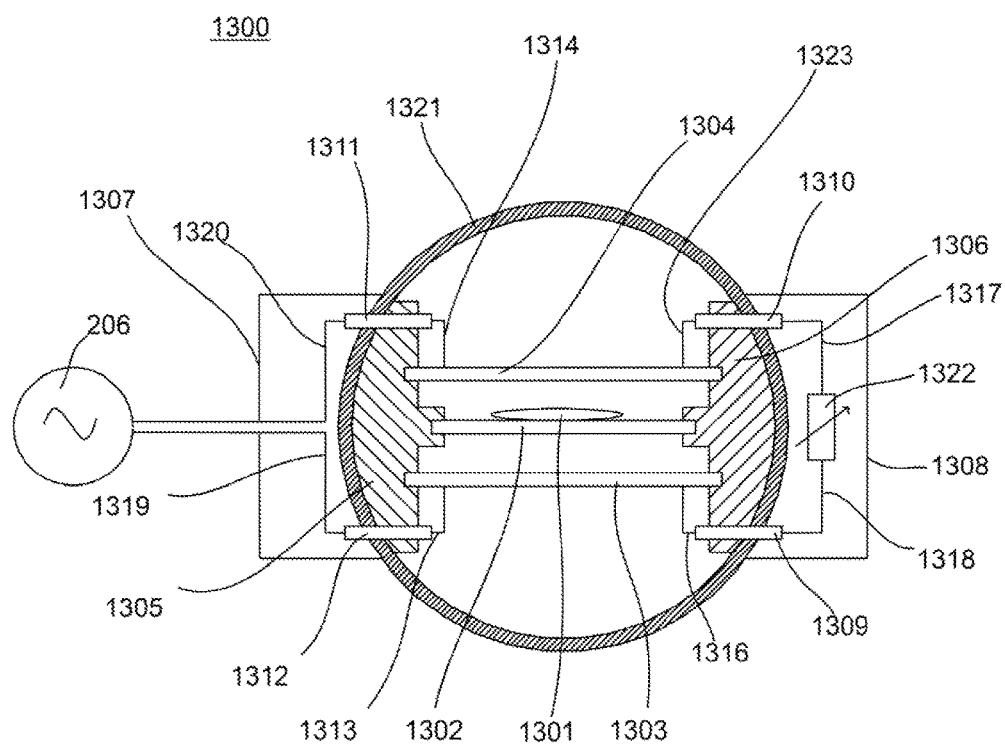
FIG. 13 is an illustration of an embodiment of a non-modal interplate microwave applicator that includes a cylindrical nonresonant enclosure.

FIG. 13 illustrates another embodiment of a non-modal interplate microwave applicator 1300. FIG. 13 shows a vertical section through a microwave applicator 1300. The microwave applicator has a cylindrical nonresonant enclosure 1321. The load 1301 to be treated is placed on a load holder 1302. The load holder 1302 is held in place by a supporting structure 1305 and 1306 preferably made of a microwave transparent material such as PTFE. The supporting structure is also holding the applicator plates 1303 and 1304 in place. The microwave source 206 is connected to the applicator through transmission lines 1319, 1320, 1313 and 1314. The transmission lines are guided through the enclosure via connectors 1311 and 1312. A tuning device 1322 is attached to the applicator through transmission lines 1317, 1318, 1316, 1323 and connectors 1309 and 1310. A microwave tight shield 1307 and 1308 may be included to prevent the transmission lines and the tuning device from radiating any microwaves to the surroundings. The microwave heating system 1300 can be equipped with metallic lids attached to both ends of the nonresonant enclosure forming a pressure tight compartment inside the enclosure.

Figure 14A:
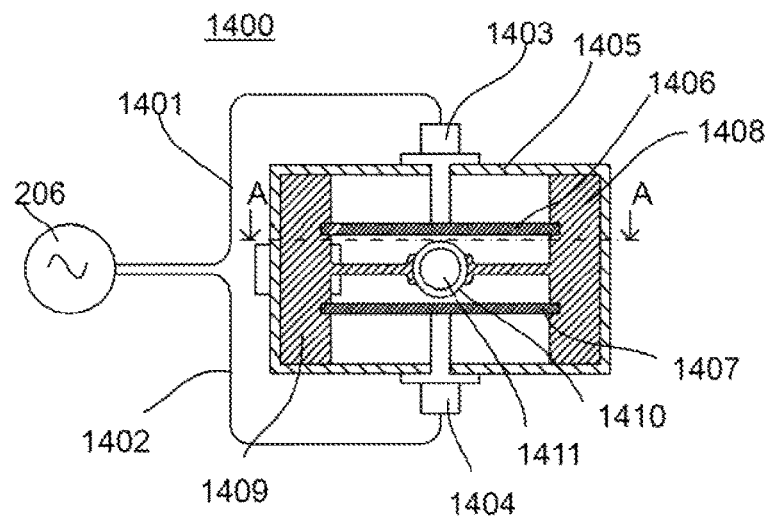
FIGS. 14A-14B are illustrations of an embodiment of a non-modal interplate microwave applicator that includes a flow reactor.

FIG. 14A shows a cross sectional view of a non-modal interplate microwave applicator 1400 that includes a flow reactor 1410 positioned between plates 1406 and 1407 of the non-modal interplate microwave applicator. The flow reactor 1410 can be made of any suitable material. For example if flow reactor 1410 is made of a microwave transparent material such as glass or PTFE, then the load will heated directly by the microwave energy. If the flow reactor 1410, i.e. load holder, is made of a microwave absorbent material, then the load may also be indirectly heated by the heating of the load holder, e.g. flow reactor 1410. The flow reactor 1410 is held by a supporting structure 1408 and 1409 which also holds the applicator plates 1406 and 1407 in a fixed position. The supporting structure 1408, 1409 and the flow reactor 1410 are surrounded by the nonresonant enclosure 1405.

Figure 14B:
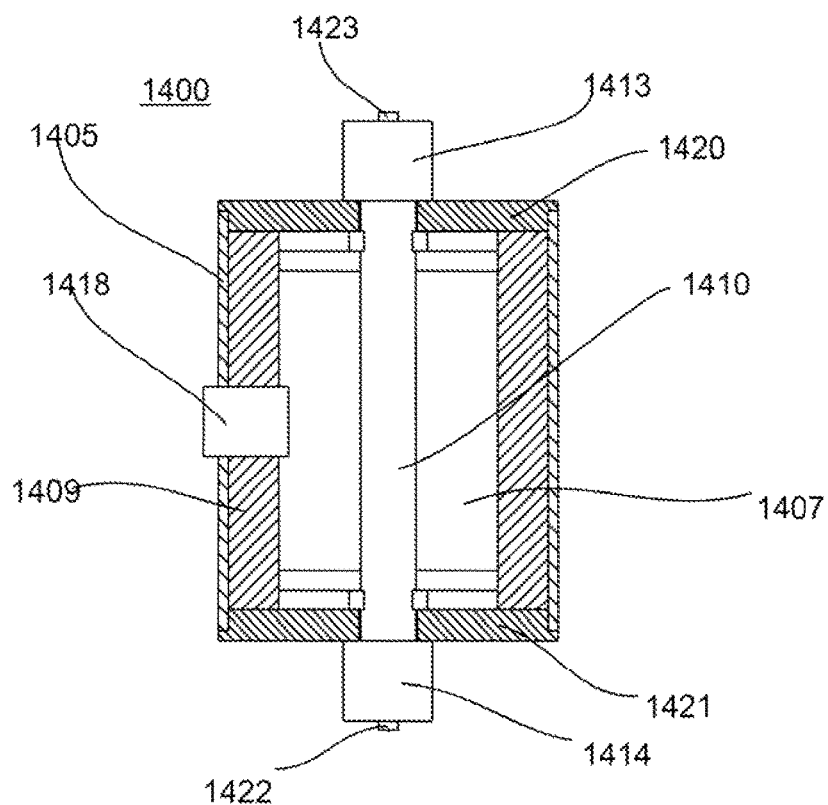
Figure 15A:
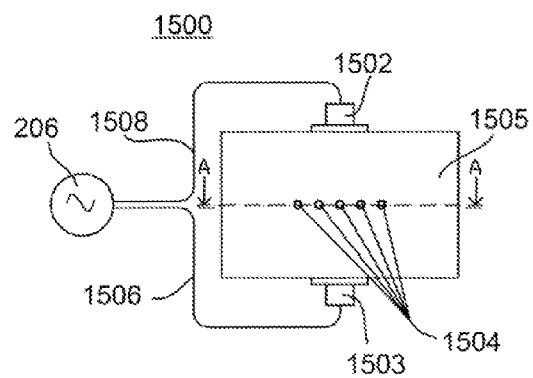
FIGS. 15A-15D are illustrations of an embodiment of a non-modal interplate microware applicator that includes capillary tubing type flow reactors.
Figure 15B:
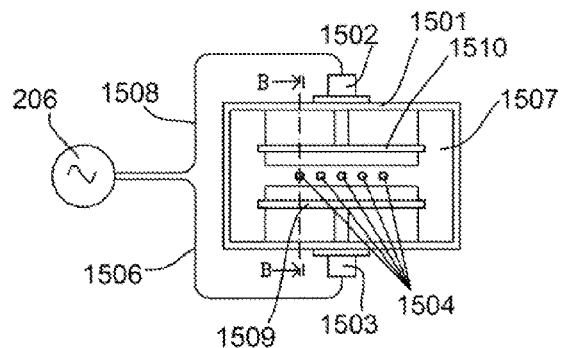
Figure 15D:
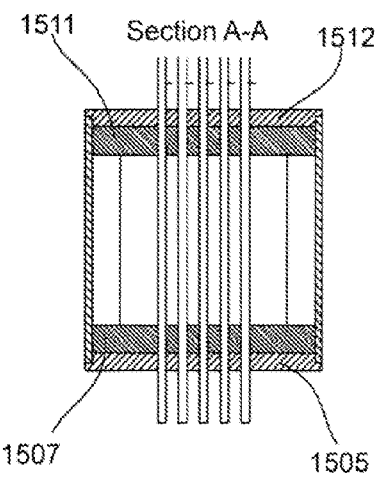
Figure 15C:
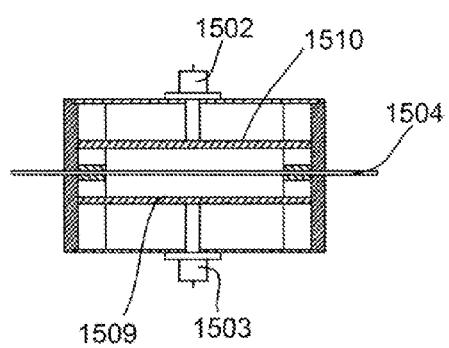

FIG. 14B illustrates a top-down view of nonresonant interplate microwave applicator 1400. Certain elements described and illustrated in FIG. 14A are not showing in FIG. 14B in order to illustrate detail from the top-down view. For example, top plate 1406, microwave source 206, connectors 1403, 1403 and transmission line 1402 are shown and described in FIG. 14A and are not shown again in FIG. 14B. The nonresonant enclosure 1405 is made of a conducting material and closed in both ends with metallic lids 1420 and 1421 as shown in FIG. 14B. The flow reactor extends through the lids on each side and is terminated with an end piece 1413 and 1414 at each end. The end pieces have a tubing connection 1422, 1423 for connecting a tube at each side of the flow reactor. The tubes are in fluid connection with the flow reactor. By attaching a pump to one end of the flow reactor and a collection vessel at the other end a reaction mixture (load) can be pumped through the reactor and thereby exposed to microwaves. The temperature of the reaction mixture can be measured by a temperature measuring device inserted into the flow reactor or by using an infrared pyrometer 1418 measuring the temperature on the surface of the flow reactor. The flow reactor 1410 can be designed to withstand extreme high pressures from 2 MPa to 500 MPa or more. The flow can be continuous or intermittent in the system. In another embodiment, and as another example, a microwave heating system 1500 as shown in FIG. 15A-15D may be provided. FIG. 15A shows a microwave heating system comprising of 5 capillary tubing in a nonresonant enclosure 1501. FIG. 15B shows a view of the microwave heating system 1500 without the lid 1505. FIG. 15C shows a microwave heating system comprising capillary tubes 1504 as flow reactors. The capillaries are held in position by a supporting structure 1507, 1511 made of a microwave transparent material. The applicator plates 1509, 1510 are also held in position by the supporting structure 1507 and 1511. The microwaves are fed to the applicator through the connectors 1502, 1503 and transmission lines 1506, 1508 which are connected to the microwave source 206. The whole structure is surrounded by a nonresonant enclosure 1501. The enclosure 1501 is closed at each end with metallic lids 1505, 1512 to prevent the microwaves from propagating outside the enclosure.

Figure 16:
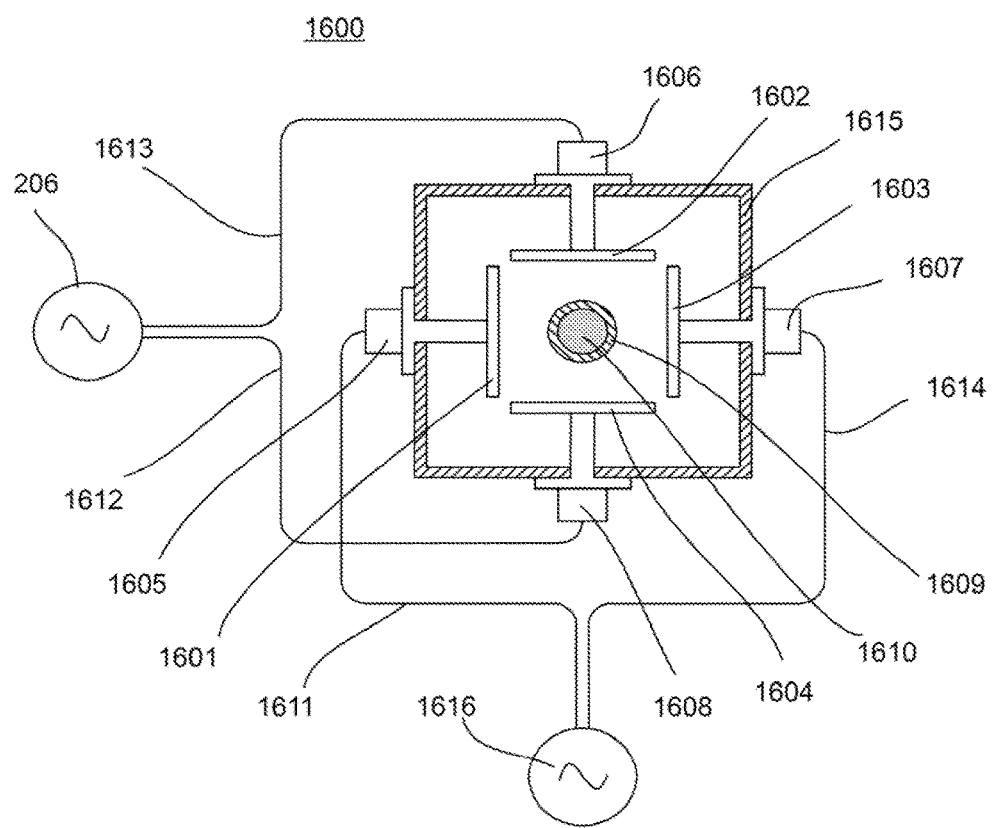
FIG. 16 is an illustration of an embodiment of a non-modal interplate microwave applicator with orthogonal plate pairs arranged around a load.

In another embodiment, and as another example, a microwave heating system 1600 as shown in FIG. 16 may be provided. FIG. 16 shows a microwave heating system comprising two pairs of applicator plates 1601, 1603 and 1602, 1604. The two systems are fed from two separate microwave sources 206 and 1616. The load to be treated 1610 can be contained in a reaction vessel 1609 permanently or replaceable mounted in the nonresonant enclosure 1615. The reaction vessel can be a flow reactor for treating flowing loads like reaction mixtures. The two pairs of applicator plates are mounted 90° rotated relative to each other. It should be noted that the rotation can be made to any angle and the geometric form of the plates can be other than shown in FIG. 16. The plates are fed via transmission lines 1612, 1613 and 1611, 1614 and through the connectors 1606, 1608 and 1605, 1607. The nonresonant enclosure is closed in each end with metallic lids (see FIG. 6). In case of a flow reactor, the lid has openings for the flow reactor tube to extend outside the lids.

Figure 17:
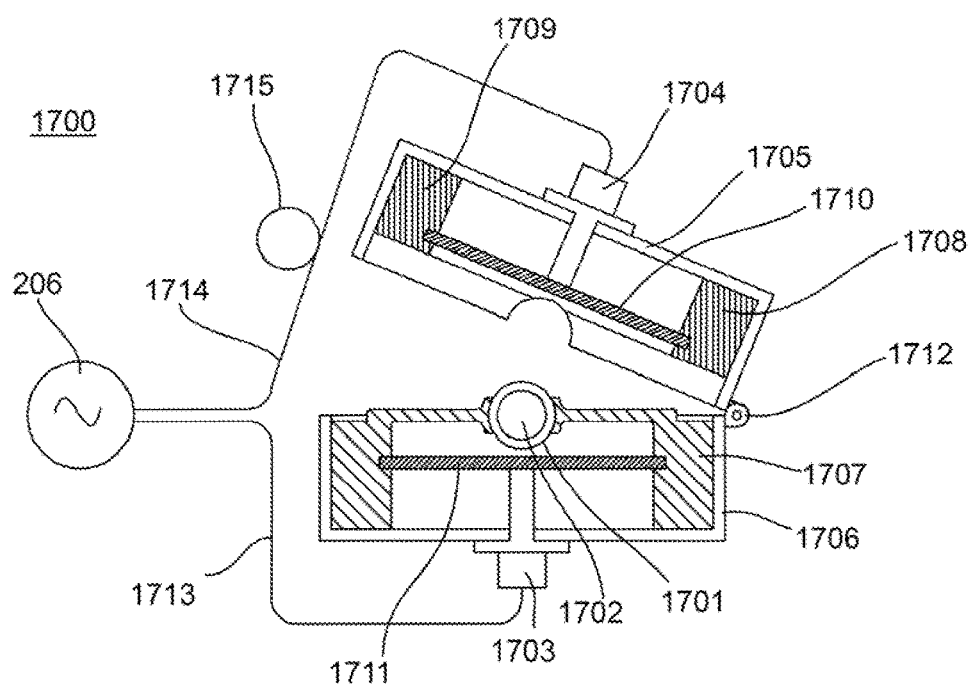
FIG. 17 is an illustration of an openable embodiment of a non-modal interplate microwave applicator.

In another embodiment, and as another example, a microwave heating system 1700 as shown in FIG. 17 may be provided. FIG. 17 shows a microwave heating system comprising an open able nonresonant enclosure 1705 and 1706. The two halves are held together by a hinge 1712. The open structure makes it easy and convenient to insert and extract the load and the load holder to and from the system. The load 1702 can be contained in a consumable type of load holder for one time use where the treated matter is inserted into an ampoule 1701 or similar structure. The system 1700 can also be used when a long structure such as a long flow reactor is to be heated and it is not possible, or inconvenient, to mount the reactor without opening the system 1700. The reaction vessel 1701 is held in place by a holding structure 1707 which also holds the lower applicator plate 1711 in place. The upper applicator plate 1710 is held in place by the structure 1708, 1709. The transmission line 1714 is made as a flexible component 1715 in order to make it possible to open the upper part of the nonresonant enclosure 1705. The microwaves are fed from the microwave source 206 to the applicator plates through the transmission lines 1714, 1713 and through the connectors 1703 and 1704. The nonresonant enclosure is formed by the two enclosure halves 1705 and 1706 in closed position and closed at each end with metallic lids (see FIG. 6). In case of a flow cell, the lid has openings for the tube to extend outside the lids [missing 1715 still].

Figure 18:
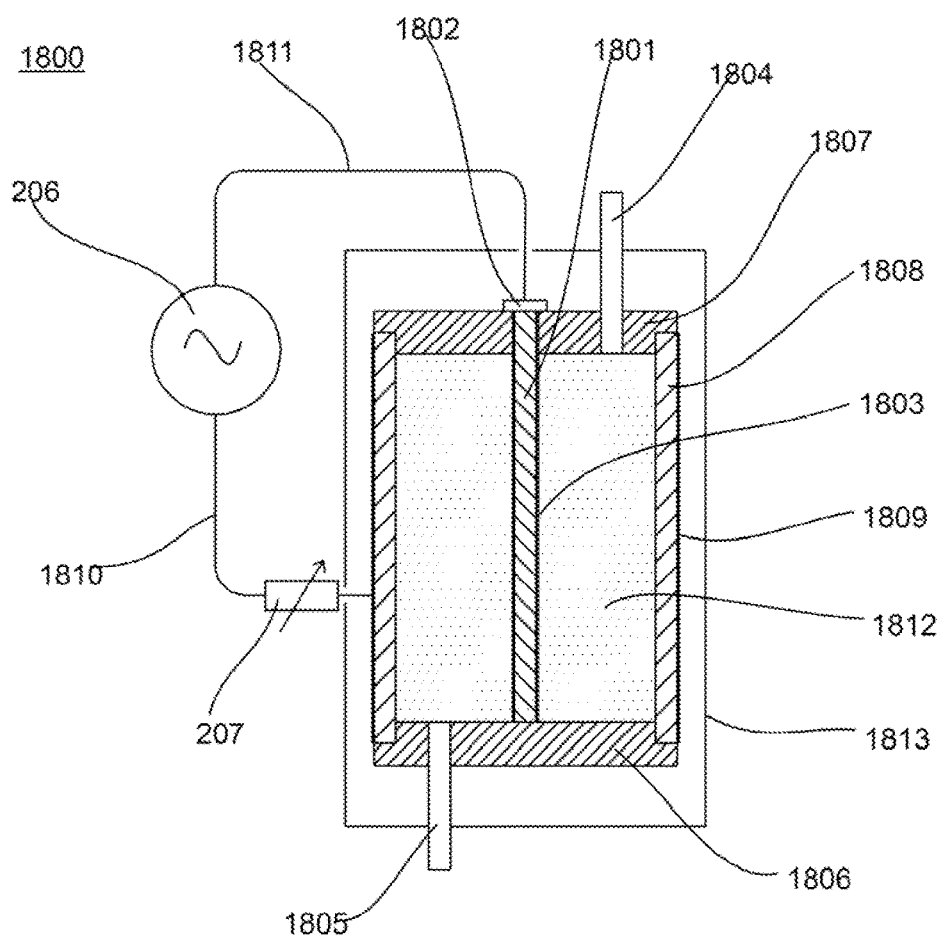
FIG. 18 is an illustration of a cylindrical embodiment of a non-modal interplate microwave applicator that includes a reaction vessel with an inlet and an outlet.

In another embodiment, and as another example, a microwave heating system 1800 as shown in FIG. 18 may be provided. FIG. 18 shows a microwave heating system comprising a cylindrical applicator with an inner cylinder 1801 and an outer cylinder 1809. The load to be treated is contained in a reaction vessel consisting of an outer cylindrical member 1808 and a lid 1806 and 1807 attached to each end of the cylindrical member 1808. The cylindrical member 1808 is made of microwave transparent materials such as glass or PTFE. The lids 1806 and 1807 can be made of any suitable material. The outer cylindrical applicator part 1809 can be either a separated component or an integrated part of the cylindrical member 1808. The outer cylinder 1809 can typically be integrated with 1808 through metal deposition on the surface of the cylindrical part 1808. The inner cylinder 1801 can be made of a metallic material with a protecting layer 1803 of the surface. The protecting layer is made of a microwave transparent material and chemical resistant to the solvent used in the applied treatment process. To feed the reaction vessel with reaction mixture (load) 1812, both lids 1806 and 1807 have openings 1804 and 1805 to be used as an inlet on one side and an outlet on the other side. A reaction mixture can be pumped through the reaction vessel. When both openings 1804 and 1805 are closed the system 1800 can be used as a batch reactor with a stationary load 1812 in the reaction vessel. The reaction vessel is surrounded by a nonresonant enclosure 1813 to create appropriate boundary conditions to contain the electromagnetic field within the enclosure 1813. The microwaves are fed from the microwave source 206 to the cylindrical applicators through the transmission lines 1810 and 1811 and through the connector 1802. A tuning device 207 can be attached to the system 1800 between the microwave source 206 and the outer cylinder 1809. The space between the enclosure and the reaction vessel can be pressurized to balance an internal over pressure inside the reaction vessel. The internal pressure in the reaction mixture can either be generated from the chemical reaction itself or by adding a restrictor in a flowing system to generate the internal pressure.

Figure 19:
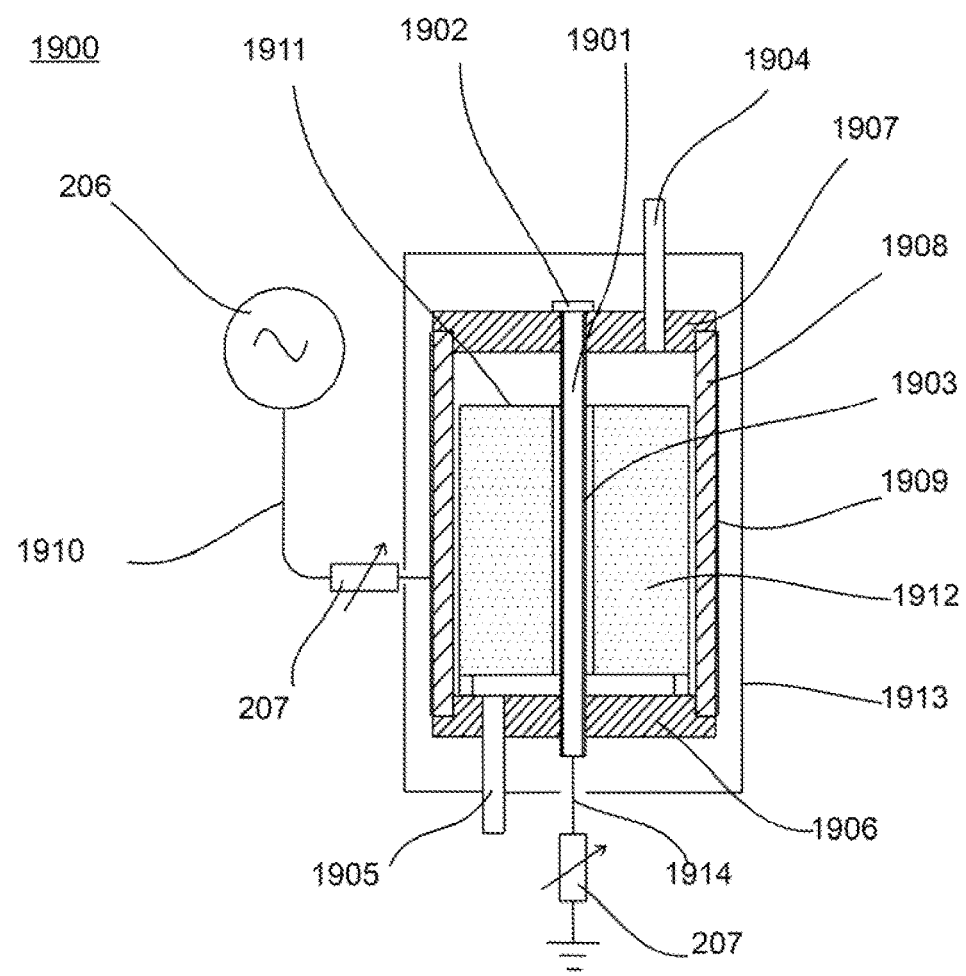
FIG. 19 is an illustration of another cylindrical embodiment of a non-modal interplate microwave applicator that includes a reaction vessel with an inlet and an outlet.

In another embodiment, and as another example, a microwave heating system 1900 as shown in FIG. 19 may be provided. FIG. 19 shows a microwave heating system comprising a cylindrical applicator with an inner cylinder 1901 and an outer cylinder 1909. The load to be treated 1912 is contained in a reaction vessel 1911 placed in the compartment consisting of an outer cylindrical member 1908 and a lid 1906 and 1907 attached to each end of the cylindrical member 1908. The cylindrical member 1908 is made of microwave transparent materials such as glass or PTFE. The lids 1906 and 1907 can be made of any suitable material. The reaction vessel 1911 is made of a microwave transparent material. The outer cylindrical applicator part 1909 can be either a separated component or an integrated part of the cylindrical member 1908. The outer cylinder 1909 can typically be integrated with 1908 through metal deposition on the surface of the cylindrical part 1908. The inner cylinder 1901 can be made of a metallic material with a protecting layer 1903 of the surface. The protecting layer is made of a microwave transparent material and chemical resistant to the solvent used in the applied treatment process. The reaction vessel 1911 with reaction mixture (load) 1912 is placed inside the outer cylinder 1908 by removing either the upper lid 1907 or the lower lid 1906. The reaction vessel 1911 is filled with reaction mixture 1912 before inserted into the outer cylinder 1908. Both lids 1906 and 1907 have an opening 1904 and 1905 to be used as inlet and outlet cooling media, inert gas or to pressurize the environment inside the nonresonant enclosure 1913. The reaction vessel is surrounded by a nonresonant-enclosure 1913 to create appropriate boundary conditions to contain the electromagnetic field within the enclosure 1913. The microwaves are fed from the microwave source 206 to the outer cylindrical applicator member through the transmission line 1910. A tuning device 207 can be attached to the system 1900 between the microwave source 206 and the outer cylinder 1909 or between the inner cylinder and ground connection via transmission line 1914. The space between the enclosure and the reaction vessel can be pressurized to balance an internal over pressure inside the reaction vessel. The internal pressure in the reaction mixture can be generated from the chemical reaction.

Figure 20:
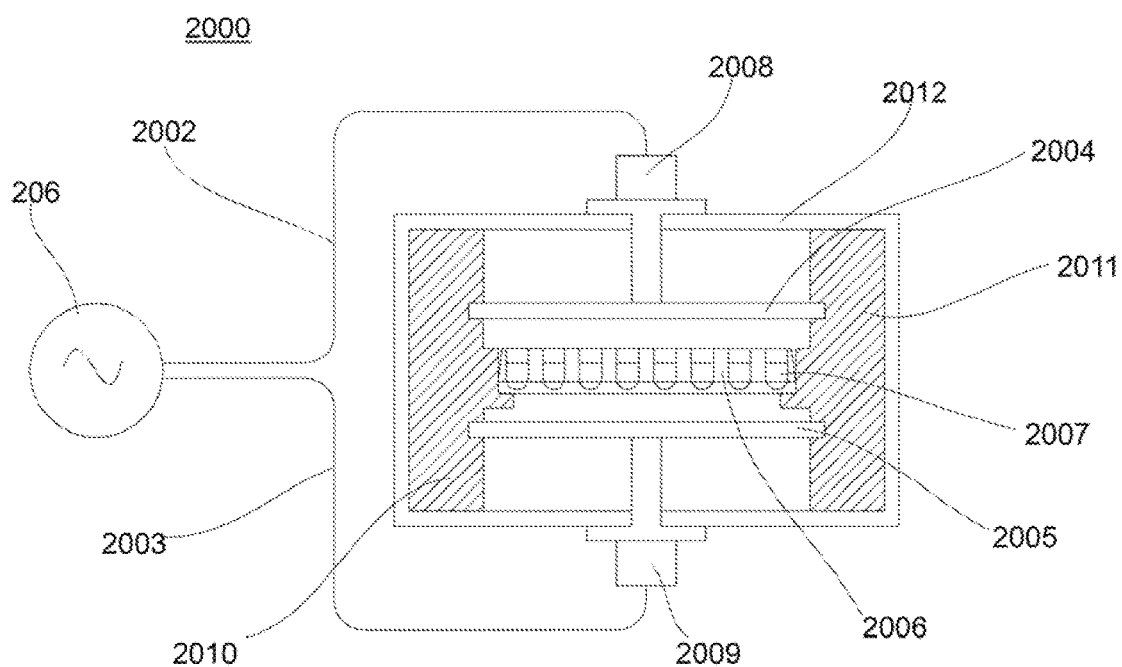
FIG. 20 is an illustration of an embodiment of a non-modal interplate microwave applicator configured to receive a multi-well load.

In another embodiment, and as another example, a microwave heating system 2000 as shown in FIG. 20 may be provided. FIG. 20 shows a microwave heating system comprising a holder 2010 and 2011 for a micro titer plate 2006 or a similar array structure. The micro titer plate comprises the load 2007 to be treated. The microwaves are fed from the microwave source 206 to the applicator plates 2004 and 2005 through the transmission lines 2002, 2003 and through the connectors 2008 and 2009. The nonresonant enclosure 2012 is closed at each end with metallic lids (see FIG. 15).

Figure 21:
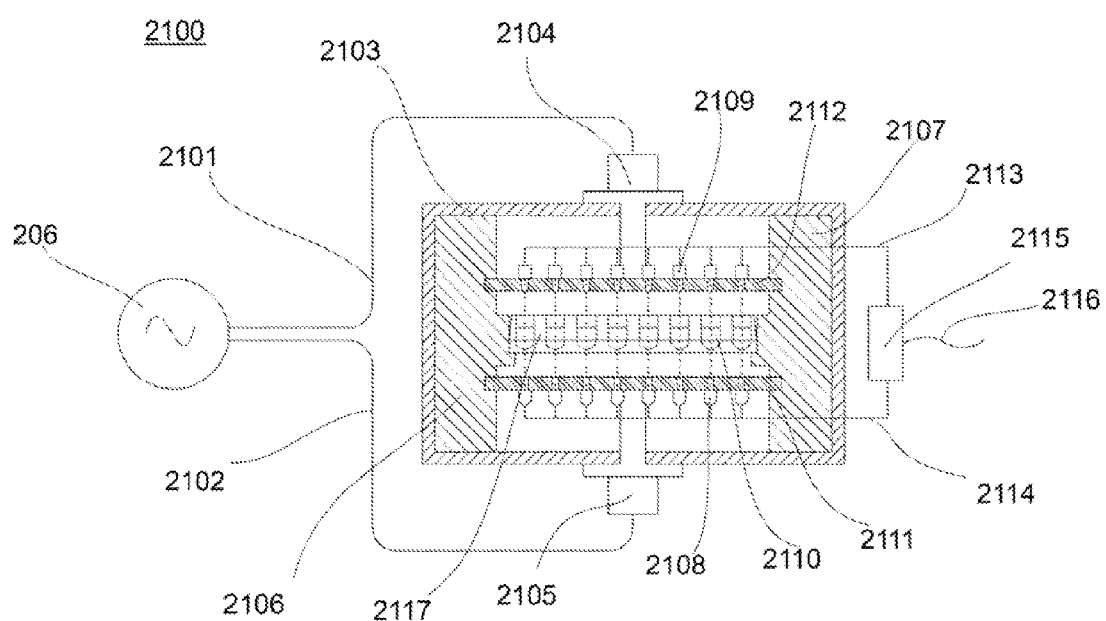
FIG. 21 is an illustration of another embodiment of a non-modal interplate microwave applicator that includes a load monitoring system and configured to receive a multi-well load.

In another embodiment, and as another example, a microwave heating system 2100 as shown in FIG. 21 may be provided. FIG. 21 shows a microwave heating system comprising a holder 2106 and 2107 for a micro titer plate 2117 or a similar array structure enclosed in non resonant enclosure 2103. The micro titer plate is containing the load 2110 to be treated. The microwaves are fed from the microwave source 206 to the applicator plates 2111 and 2112 through the transmission lines 2101, 2102 and through the connectors 2104 and 2105. The nonresonant enclosure 2103 is closed at each end with metallic lids (see FIG. 6). The system 2100 has a monitoring system containing an array of transmitters 2109 and a similar array of receivers 2108 mounted in the opposite side of the micro titer plate. The transmitter can transmit any type of electromagnetic signal such as ultra violet, infra red, x-ray, laser, etc., and the receiver can be any type of detector detecting the transmitted signal. The transmitter and receiver are connected to a control unit 2115 through a signal line 2113 and 2114. The control unit either evaluates the signals or just transmits them to a computer via connection 2116 for further calculations. The signal can be used to monitor and/or control a chemical reaction or a diagnostic process.

Figure 22:
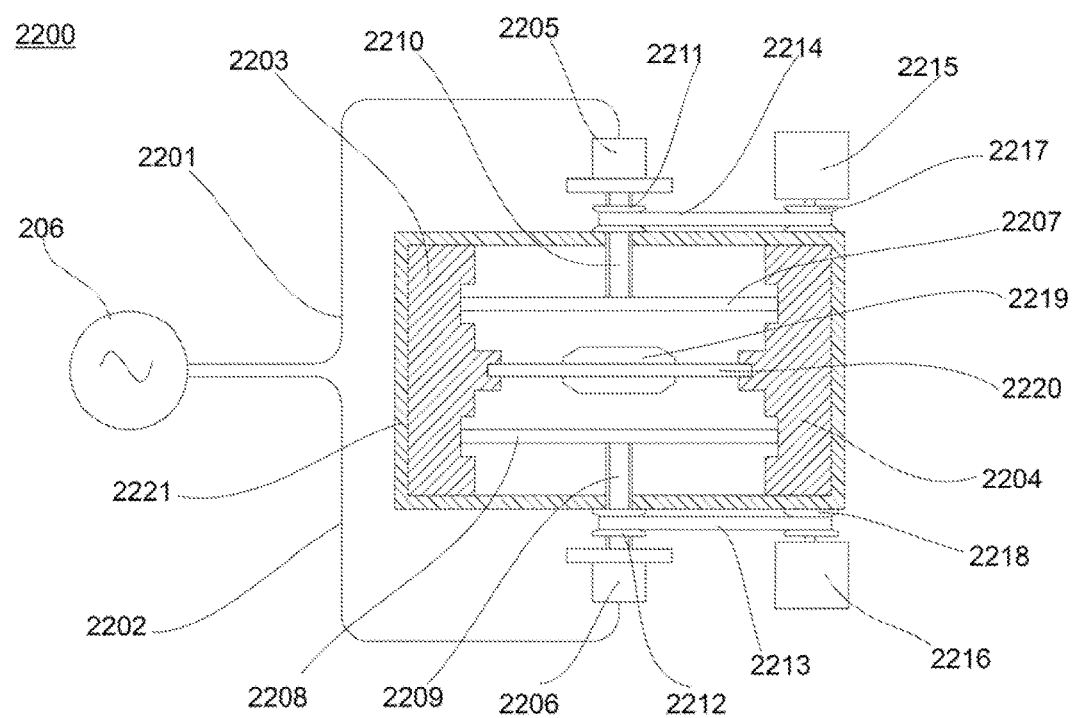
FIG. 22 is an illustration of an embodiment of a non-modal interplate microwave applicator that includes adjustable applicator plates.

In another embodiment, and as another example, a microwave heating system 2200 as shown in FIG. 22 may be provided. FIG. 22 shows a microwave heating system with mechanically adjustable applicator plates 2207 and 2208. By adjusting the plates the impedance matching can be changed for the applicator and thereby tuned to achieve optimal heating conditions. The load 2219 to be treated is attached to a load holder 2220 which can be a microscope slide. The load holder is held in position by a holding structure 2203 and 2204. The applicator plates are individually adjustable by rotating the combined belt pulley and drive pulley 2211 and 2212. By rotating the pulley the nut will force the threaded shaft 2209 and 2210 to move the applicator plate up or down relative to the load and the other applicator plate. The pulley is rotated through a timing belt 2213 and 2214 connected to drive nuts 2217 and 2218 driven by motor 2215 and 2216. The microwaves are fed from the microwave source 206 to the applicator plates 2207 and 2208 through the transmission lines 2201, 2202 and through the connectors 2205 and 2206. The nonresonant enclosure 2221 is closed at each end with metallic lids (see FIG. 6).

Figure 23A:
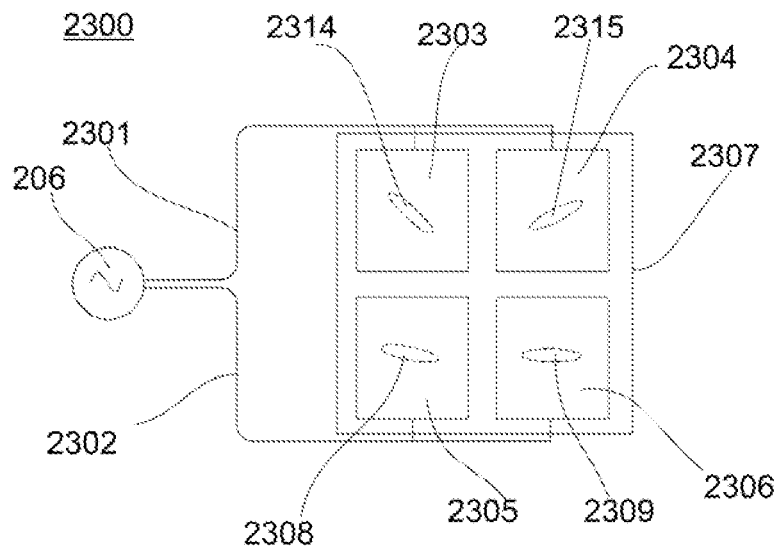
FIGS. 23A-23B are illustrations of an embodiment of a microwave heating system that includes an array of non-modal interplate microwave applicator plates.
Figure 23B:
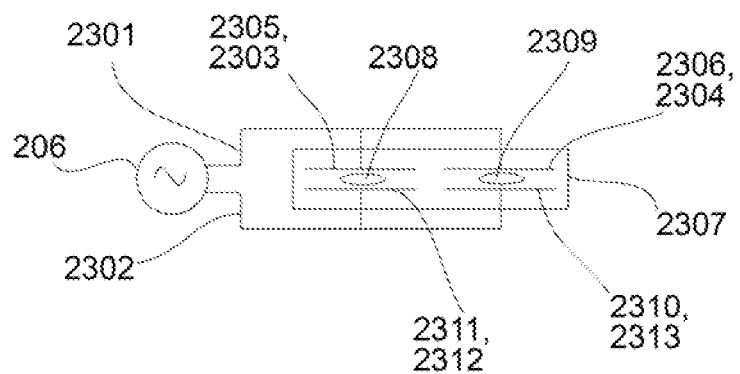

In another embodiment, and as another example, a microwave heating system 2300 as shown in FIG. 23 may be provided. FIG. 23 shows a microwave heating system comprising an array of applicator plates 2303, 2304, 2305, 2306 and 2310, 2311, 2312, and 2313. The load 2308, 2309, 2314, and 2315 to be treated is placed between each pair of applicator plates. A nonresonant enclosure 2307 is surrounding all applicator plates. The microwaves are fed from the microwave source 206 to the applicator plates through the transmission lines 2301, 2302.

Figure 24:
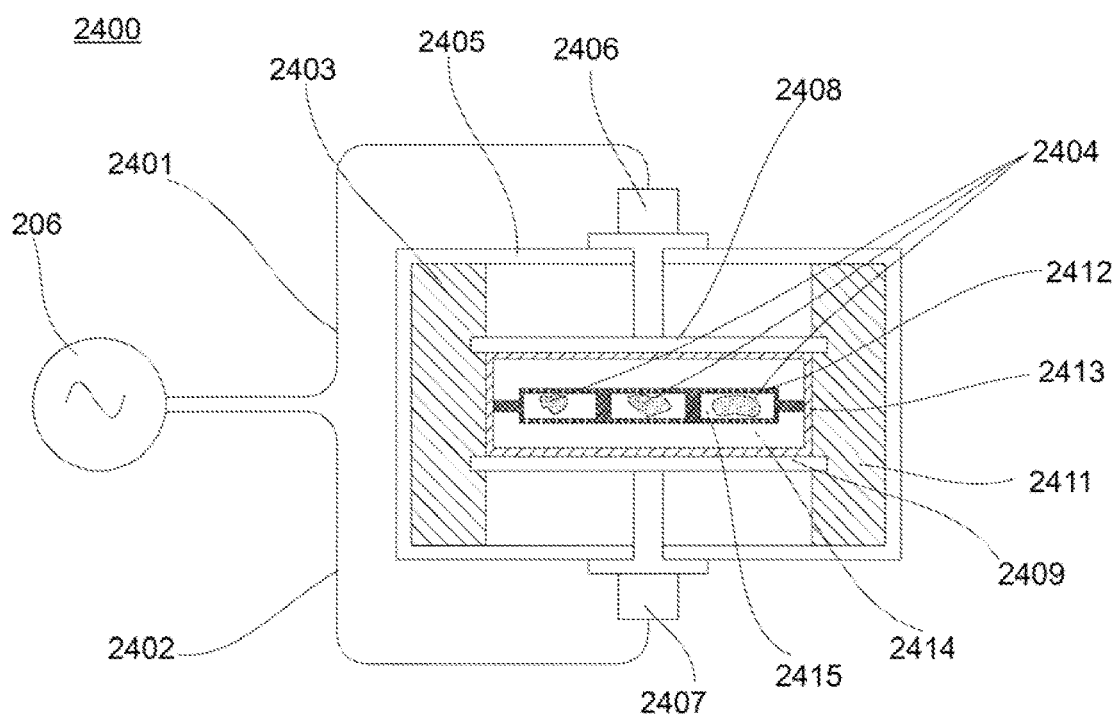
FIG. 24 is an illustration of a multi-sample processing system that includes multiple non-modal interplate microwave applicators

In another embodiment, and as another example, a microwave heating system 2400 as shown in FIG. 24 may be provided. FIG. 24 shows a microwave heating system comprising a holder 2412 for tissue samples 2404. The holder 2412 is submerged into a vessel 2413 filled with a tissue treatment liquid 2414. The tissue holding structure 2412 has openings 2415 in the structure to allow the treatment liquid to freely pass through the structure and circulate around the tissue samples. The holding structure and the vessel are made of any microwave transparent material. The vessel can be equipped with an inlet and outlet opening at the bottom to make it possible to fill and drain the vessel automatically with a pump system. The pump system can also be used for circulation of the liquid in the vessel. The vessel and the applicator plates are held in position by a holding structure 2403 and 2411. The microwaves are fed from the microwave source 206 to the applicator plates 2408 and 2409 through the transmission lines 2401, 2402 and through the connectors 2406 and 2407. The nonresonant enclosure is closed at each end with metallic lids (see FIG. 15).

Figure 25:
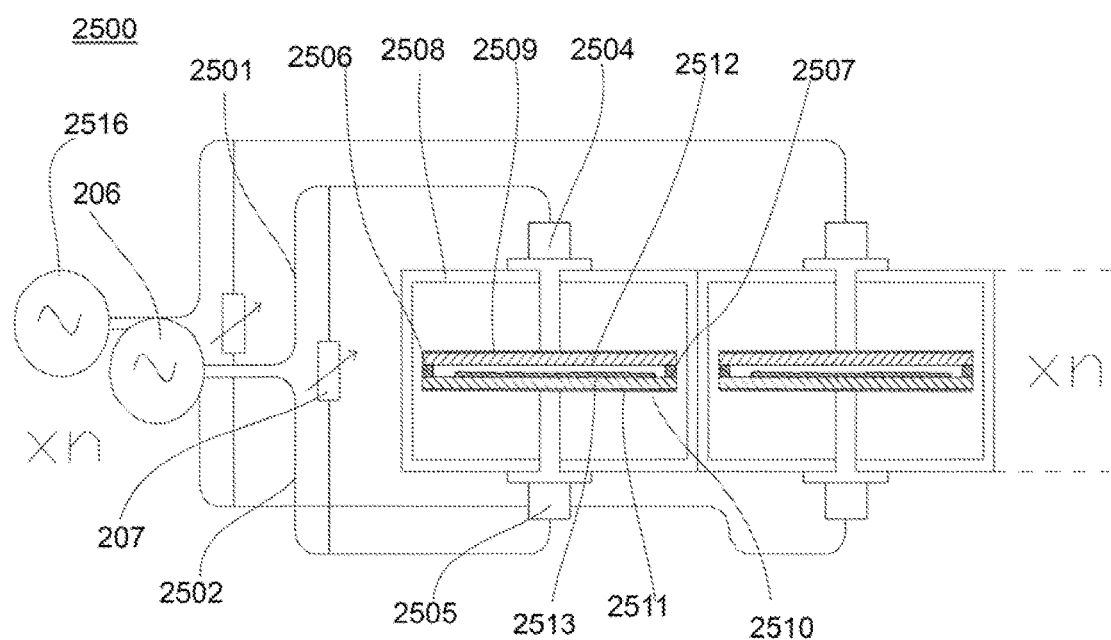
FIG. 25 is an illustration of another embodiment of a multi-sample processing system that includes multiple non-modal interplate microwave applicators having separate microwave sources.
Figure 26:
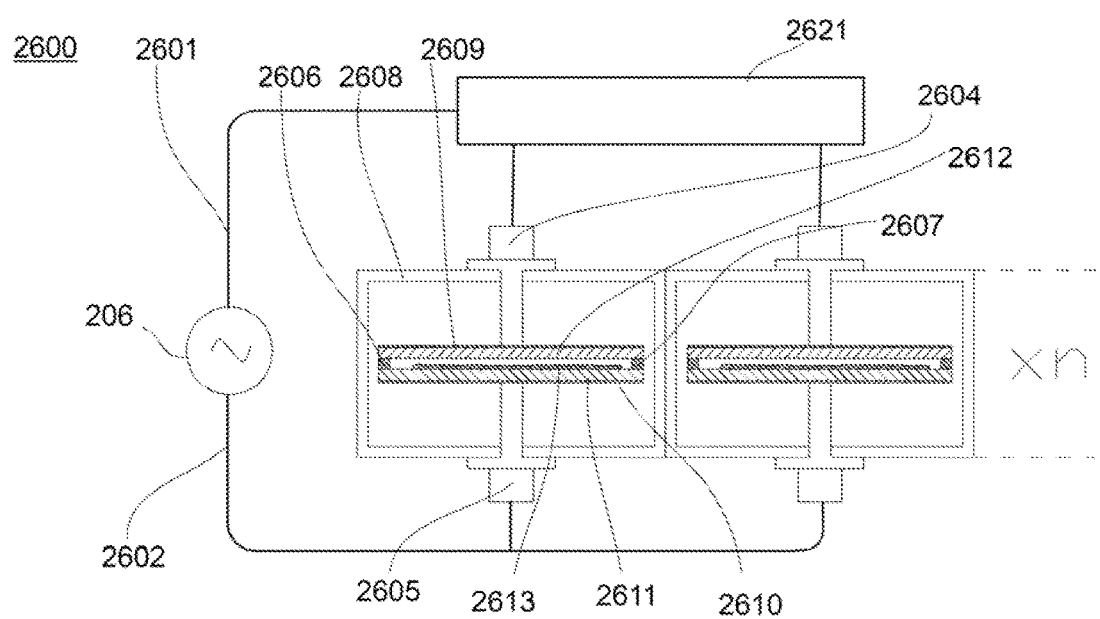
FIG. 26 is an illustration of another embodiment of a multi-sample processing system that includes multiple non-modal interplate microwave applicators having a multiplexed microwave source.

In another embodiment, and as another example, a microwave heating system 2500 as shown in FIG. 25 may be provided. FIG. 25 shows a microwave heating system comprising a plurality of applicators in the same system. The number of applicators can be repeated many times and be run one at a time, in series or in parallel. It shall be noted that any of the described applicators and systems can be configured with a plurality of applicators as described in FIG. 25. The system 2500 comprises n channels each having a pair of applicator plates 2509, 2510 where the applicator plates are an integrated part of a glass slab 2511, 2512. The glass slab can for example be a microscope slide. The sample 2513 is placed on one of the glass slabs. The two glass slabs are separated by two spacers 2506, 2507 and thereby creating a small compartment containing the load. Another spacer can be placed perpendicular to 2506 and 2507 and at the bottom and top of the compartment and thereby creating a closed compartment which can be filled with a liquid or gas. The liquid or gas can be a reagent aiming at treating the load 2513. The microwaves are fed from the microwave source 206 to the applicator plates 2509 and 2510 through the transmission lines 2501, 2502 and through the connectors 2504 and 2505. A tuning device 207 can be added to each applicator. The nonresonant enclosure 2508 is closed at each end with metallic lids (see FIG. 15) [Missing description of 2516 second microwave source].

It also should be noted that the various metallic structures described herein may be formed of any type of metal or a composite thereof. For example, metals such as copper, aluminum, brass, steel, etc. or combinations or composites thereof may be used.

The system can have a separate microwave source 206 for each applicator, as described in FIG. 25 or use one microwave source 206 and a distributing system 2621 that distributes the power equally to the number of applicators used or on a time sharing basis where a switching device delivers a predetermined portion of a total time cycle to each applicator.

Figure 27:
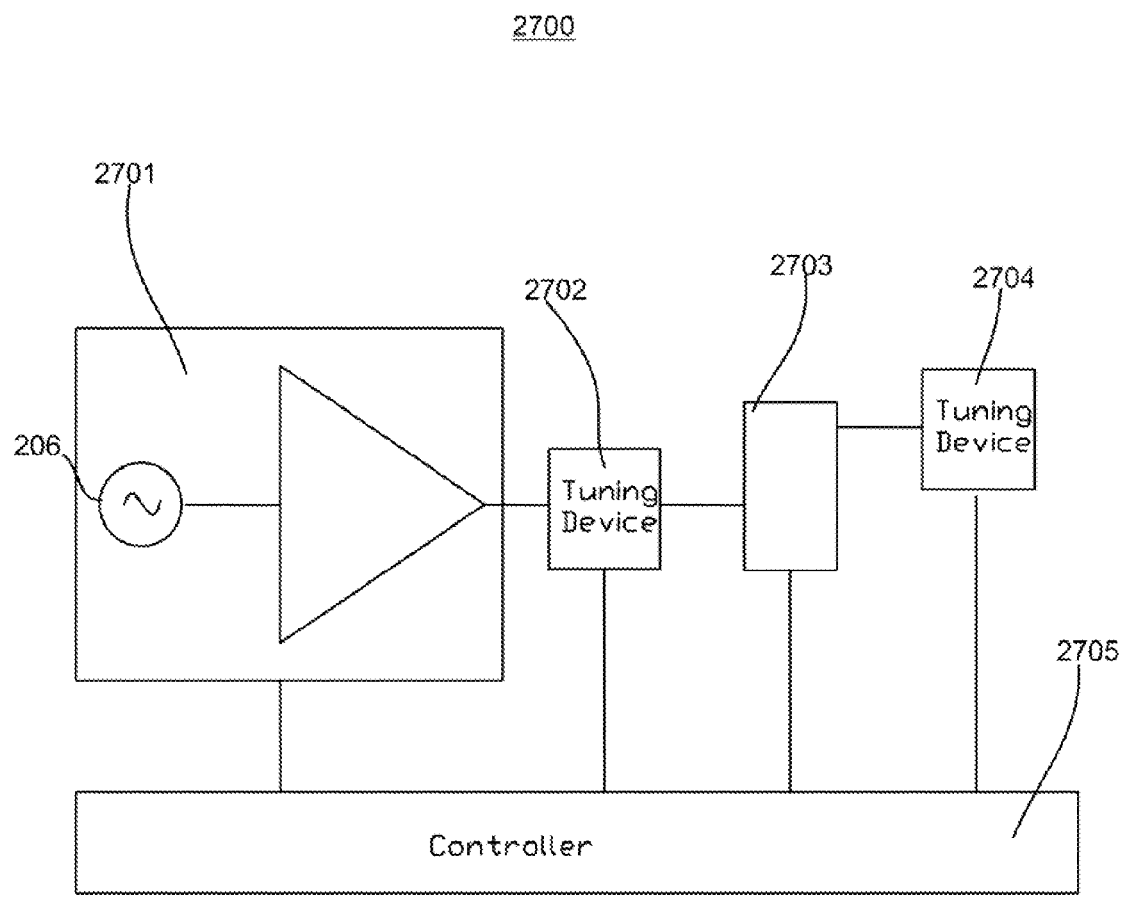
FIG. 27 is an illustration of a control system with tuning devices for controlling non-modal interplate microwave applicators.

FIG. 27 shows a system block diagram of a microwave heating system 2700 that includes a controller 2705 that can control the tuning devices 2702 and 2704 described herein to optimize the performance of the heating systems described herein. The control system 2705 is controlled by control signals from, for example, a number of sensors and measuring devices in the system as described herein. This signal can be, for example, temperature, pressure, reflected power, etc. The control system 2705 can be, for example, a finite state machine or a feedback machine. The tuning devices can 2702 and 2704 can be placed either between the microwave source 206 and the applicator 2703 or/and after the applicator 2703.

Figure 28A:
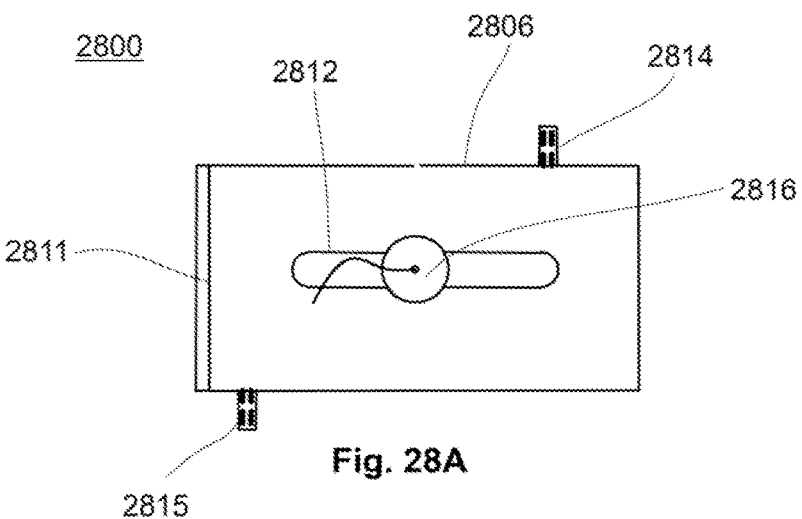
FIGS. 28A-28C are illustrations of an embodiment of a non-modal interplate microwave applicator that includes monitoring devices.
Figure 28B:
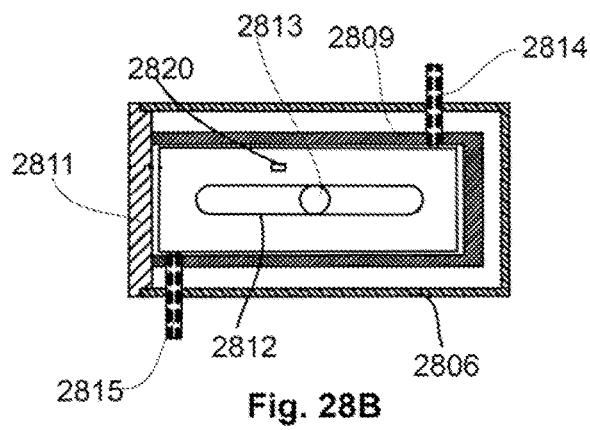
Figure 28C:
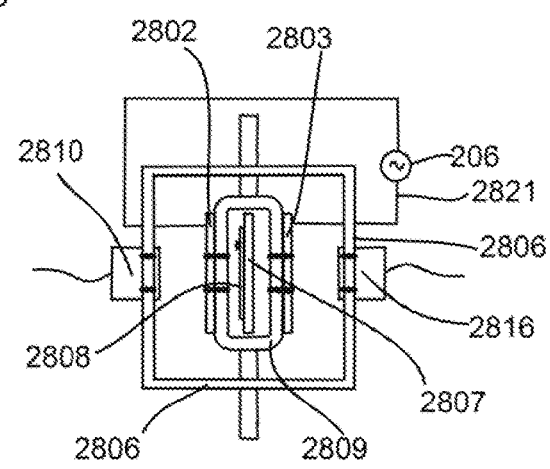

In another embodiment, and as another example, a microwave heating system 2800 as shown in FIGS. 28A, 28B and 28C may be provided. The microwave heating system 2800 includes a nonresonant enclosure 2806 constructed of metal and having an applicator consisting of the two applicator plates 2802 and 2803 therein surrounding a supporting structure 2809. However, the nonresonant enclosure 2806 may have any shape or size that fulfills the conditions for a nonresonant structure. FIG. 28B shows a cross-section of such a heating system 2800. FIG. 20F shows a view from the left without the lid 2811 on.

A metallic lid 2811 is provided to close the nonresonant enclosure 2806. The metallic lid 2811 may provide a pressure tight seal. In this embodiment, the object to be treated with microwaves, namely the load 2808 is placed on a holding structure 2807 that can be a glass slab. It should be noted that the slab may be made of any material. Moreover, the load 2808 can be of any shape or size, for example, a shape and size that fits into or onto the holding structure 2807. The supporting structure 2809 may be formed, for to receive the holding structure 2807. The holding structure 2807 can be, for example, a pre-made cassette and may have features such as built in channels for liquid flow with flow ports 2814 and 2812 that can be used to enable fluids to flow in and out. Further devices like valves, pumps, etc. may be included as an integrated part of the holding structure. The cassette can be made for diagnostic, analytical or preparative purposes. The devices 2816 and 2810 can be any type of monitoring devices measuring or monitoring process parameters such as temperature, pressure, light scattering, etc. The devices 2816 and 2810 can be arranged in a way such that one is a transmitter and one is a receiver. The transmitter sends a signal that reflects, transmits, scatters, refracts or in any other way is affected by the load and the receiver receives the affected signal from the transmitter. The signals from both devices 2816 and 2810 can, for example, be compared using any computational device and an algorithm to calculate a result. The result can be used to control the microwave heating system or generate an output signal used for diagnostic or analytic purposes. The transmitter and receiver can be in the same physical enclosure and need only access from one side of the load 2808. The transmitted signal can be radiation of any type, for example, laser, Ultraviolet (UV), Infra Red (IR), x-ray, ultrasound, etc. The receiver can be any type of device that detects, for example the change in the transmitted signal caused by the microwave treatment of the load. The supporting structure 2809 has an opening 2813 to gain access to the load for the devices 2816 and 2810. The devices 2816 and 2810 can be extended to form an array. Also, the supporting structure 2809 can be filled with a liquid 2812 such that the load 2808 is submerged or partially submerged in the liquid. It should be noted that the liquid can be part of a reaction system where the liquid contains the reactant, catalyst etc. The liquid can be exchanged for a gas. A temperature measuring device 2820 can be introduced to measure the temperature in or on the load 2808. The load 2808 and the holding structure 2807 can be, for example, a pre-made cassette with built in channels for liquid flow and functions like valves, pumps etc. as an integrated part of the holding structure 2807. The cassette can be made for diagnostic, analytical or preparative purposes. The microwaves are fed from the microwave source 206 to the applicator plates 2802 and 2803 through the transmission lines 2821.

In another embodiment, and as another example, a microwave heating system 2900 as shown in FIG. 29A-29F may be provided. FIG. 29A shows a microwave heating system comprising of a coiled capillary flow reactor in a nonresonant enclosure 2901. FIG. 29B shows a view of the microwave heating system 2900 without the lid 2905 and the supporting structure 2907. FIG. 29C shows a microwave heating system comprising a coiled capillary tube 2904 formed as a flow reactor. The flow reactors are held in position by a supporting structure 2907, 2911 made of a microwave transparent material. The applicator plates 2909, 2910 are also held in position by the supporting structure 2907 and 2911. The microwaves are fed to the applicator through the connectors 2902, 2903 and transmission lines 2906, 2908 which are connected to the microwave source 206. The whole structure is surrounded by a nonresonant enclosure 2901. The enclosure 2901 is closed at each end with metallic lids 2905 and 2912 to prevent the microwaves from propagating outside the enclosure. A temperature, e.g. IR-sensor measuring device 2913 is used to monitor and control the temperature in the flow reactor. FIGS. 29E and 29F shows other types of flow reactors that could be used in the system 2900. It should be noted that the inner diameter of the flow reactor can be from a few micrometer to several centimeters or more.

In another embodiment, and as another example, a microwave heating system 3000 as shown in FIGS. 30A and 30B may be provided. FIG. 30A shows a heating system comprising a micro structure. FIGS. 30B and 30C showing the main functions of the microstructure. FIG. 30B showing the flow path in the microstructure having an inlet section with three inlet ports 3017, 3018 and 3019 also designated 13, 12 and 11. The three inlet ports are connected to a mixing chamber 3020 for mixing the liquids fed to the inlet ports. The mixing chamber 3020 is connected to a heating portion 3021 of the microstructure where the mixed liquids are exposed to microwaves. The heating portion is connected to a separation/purification portion 3022 where the processed reaction mixture is separated or purified using technologies such as chromatography, electrophoresis, phase separation etc. The separated mixture is then fed to an analysis cell 3023 carrying out any type of analysis on the processed liquid. The analysis cell is connected to an output portion 3024 of the microstructure. FIG. 30C showing a section through the micro structure 3050 containing the flow channels 3013 manufactured in the substrate 3001. The channels are closed by bonding a second substrate 3012 to the first substrate 3001. The applicator plates 3014 and 3016 can be either separate components made of a conducting material or as an integrated part of the two substrates 3001 and 3012. The microwaves are fed from the microwave source 206 to the applicator plates 3014 and 3016 through the transmission lines 3004 and 3005 and connectors 3003 and 3007. The microstructure 3050 is held in place by a holding structure 3006 and 3010. The microstructure is surrounded by a nonresonant enclosure 3009. It should be noted that the described microstructure is just an example and any type of micro or nano structure can be used in the microwave heating system 3000. It shall also be noted that the microwave heating is not limited to one process and can be used to enhance all processes used on a micro structure. This type of applications is often referred to as "lab-on-a-chip" structures.

Figure 31A:
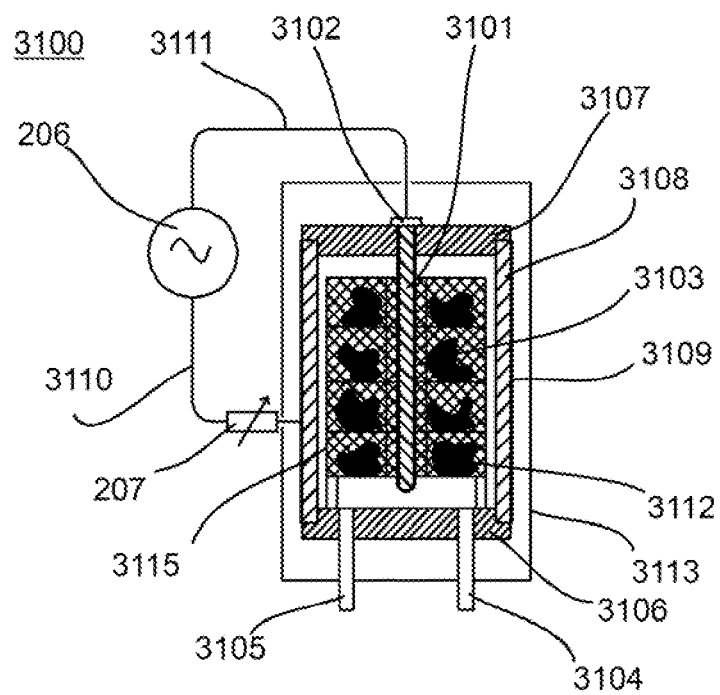
FIGS. 31A-31B are illustrations of another embodiment of multi-sample processing system that includes a cylindrical non-modal interplate microwave applicators
Figure 31B:
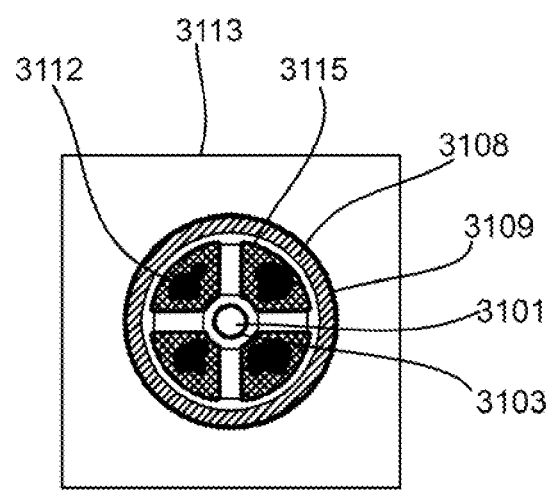

In another embodiment, and as another example, a microwave heating system 3100 as shown in FIGS. 31A and 31B may be provided. FIG. 31A shows a microwave heating system comprising a cylindrical applicator similar to the applicator described in FIGS. 18 and 10. Referring to FIG. 31A showing a microwave heating system comprising a cylindrical applicator with an inner cylinder 3101 and an outer cylinder 3109. The load 3112 to be treated is contained in a basket 3115. The basket is placed in a reaction vessel consisting of an outer cylindrical member 3108 and a lid 3106 and 3107 attached to each end of the cylindrical member 3108. The cylindrical member 3108 is made of microwave transparent materials such as glass or PTFE. The lids 3106 and 3107 can be made of any suitable material. The outer cylindrical applicator part 3109 can be either a separated component or an integrated part of the cylindrical member 3108. The outer cylinder 3109 can typically be integrated with 3108 through metal deposition on the surface of the cylindrical part 3108. The inner cylinder 3101 can be made of a metallic material with a protecting layer 3103 of the surface. The protecting layer is made of a microwave transparent material and chemical resistant to the solvent used in the applied treatment process. To feed the reaction vessel with liquid the lids 3106 have two opening 3104 and 3105 to be used as inlet and outlet for the liquid. Liquids can be pumped through the reaction vessel. When both openings 3104 and 3105 are closed the system 3100 can be used as a batch reactor with a stationary load 3112 in the reaction vessel. The reaction vessel is surrounded by a nonresonant enclosure 3113 to create appropriate boundary conditions to contain the electromagnetic field within the enclosure 3113. The microwaves are fed from the microwave source 206 to the cylindrical applicators through the transmission lines 3110 and 3111 and through the connector 3102. A tuning device 207 can be attached to the system 3100 between the microwave source 206 and the outer cylinder 3109. The space between the enclosure and the reaction vessel can be pressurized to balance an internal over pressure inside the reaction vessel. The internal over pressure can be generated to increase the boiling point of the used liquid to enhance the treatment of the load. A typical example of process in the described microwave heating system 3100 is pre-treatment of tissue for diagnostic purposes.

Figure 32:
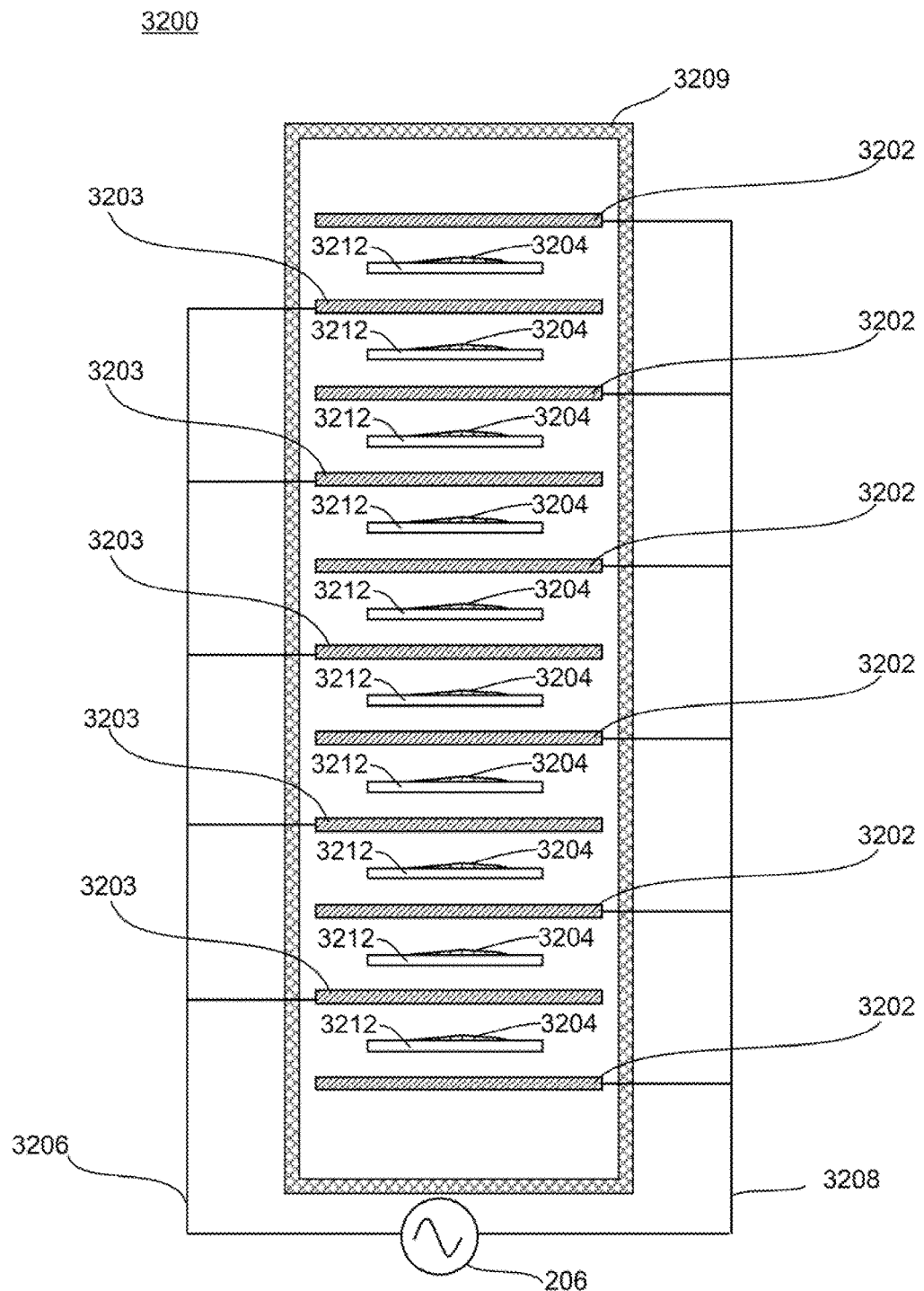
FIG. 32 is an illustration of an embodiment of a non-modal interplate microwave applicator that includes adjustable applicator plates.

FIG. 32 illustrates a multiple load interleaved plate nonmodal interplate microwave applicator 3200. By interleaving two sets of plates, a balanced non-modal interplate microwave applicator can be constructed that may be beneficial in provide a compact, balanced, symmetrical microwave heater for multiple samples. Microwave source 206 connects on one side through transmission line 3206 in parallel to plates 3203 and on another side microwave source 206 connects through transmission line 3208 in parallel to plates 3202. A load holder 3212 with a load, e.g. a tissue specimen 3204 is positioned between each set of place 3202, 3203. Thus, a very compact microwave heater that is relatively uncomplicated to construct and operated while at the same time is capable of processing a number of loads in parallel may be achieved.

Figure 33A:
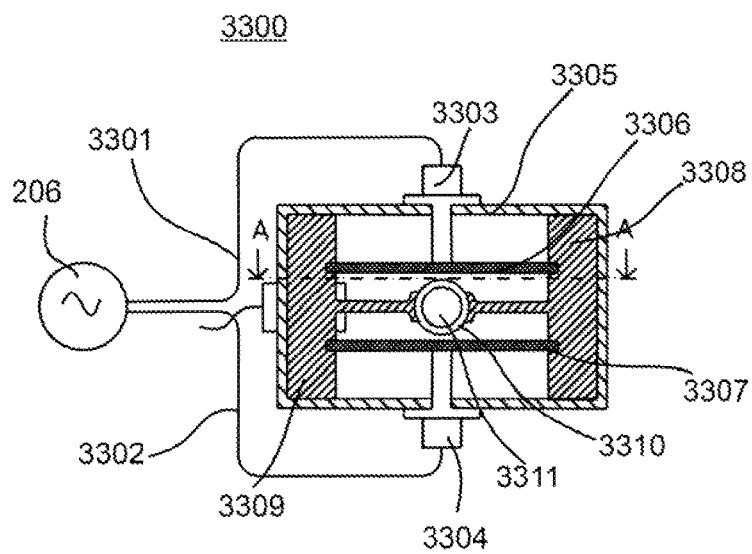
FIGS. 33A-33B are illustrations of anther embodiment of a non-modal interplate microwave applicator that includes a batch reactor.
Figure 33B:
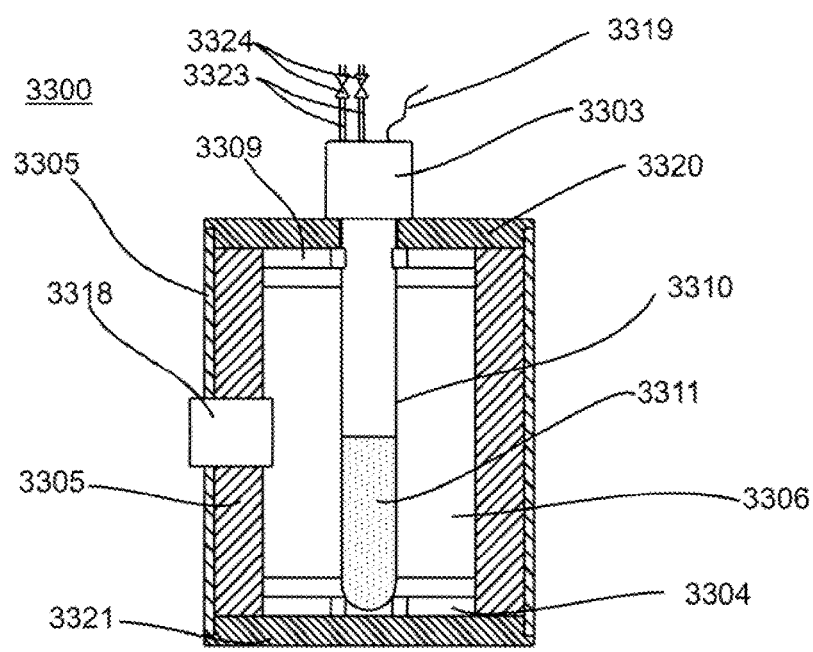

In another embodiment, and as another example, a microwave heating system 3300 as shown in FIGS. 33A and 33B may be provided. FIG. 33A shows a heating system comprising a batch reactor 3310 that is placed between the applicator plates 3306 and 3307. The batch reactor contains the reaction mixture to be microwave treated. The batch reactor can be made of any microwave transparent material such as glass or PTFE. The batch reactor is held by a supporting structure 3308 and 3309 which also holds the applicator plates 3306 and 3307 in a fixed position. The supporting structure and the batch reactor are surrounded by the nonresonant enclosure 3305. The nonresonant enclosure is made of a conducting material and closed in both ends with metallic lids 3320 and 3321. The batch reactor extends through the lids 3320 on one side and is terminated with an end piece 3313. The temperature of the reaction mixture can be measured by a temperature measuring device inserted into the reactor or by using an infra red pyrometer 3318 measuring the temperature on the surface of the batch reactor. The batch reactor 3310 can be designed to withstand extreme high pressures from 2 MPa to 500 MPa or more. The end piece 3313 can hold a pressure measuring device that can be electrical connected to a control system by cable 3319. The end piece can also contain several ports 3323 as inlet or outlet of liquids or gases to the reaction vessel. The port can have valves 3324 to close or open the access to the reaction vial. This can be used for adding reagents during a reaction or sampling of the reaction mixture to perform any type of analysis of the subtracted liquid or gas.

Figure 34A:
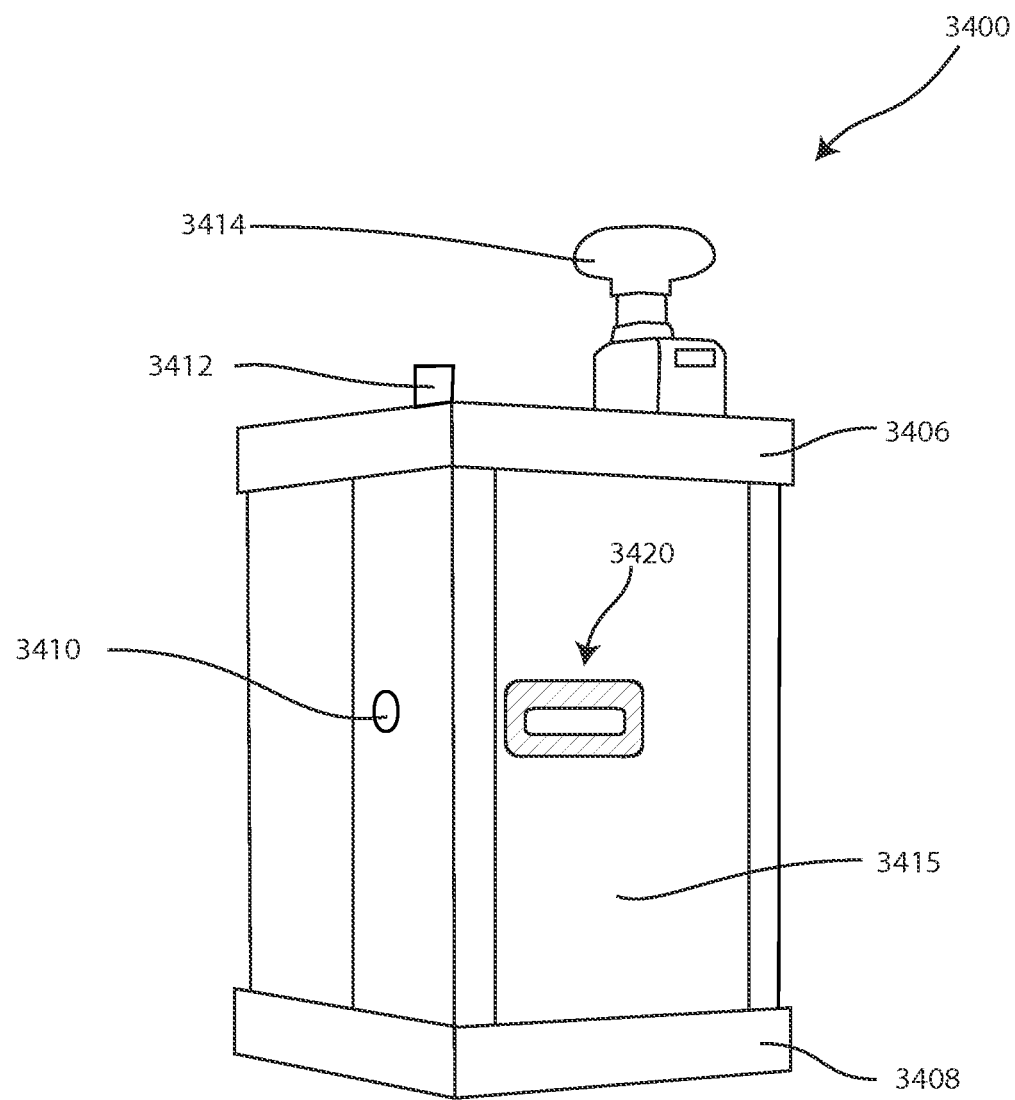
FIG. 34A illustrates a front view of an embodiment of a microwave heating system.

FIG. 34A illustrates a front view of an embodiment of a microwave heating system 3400 having a non-modal interplate microwave applicator surrounding a load. Microwave heating system 3400 includes a nonresonant enclosure 3415 In one prototype embodiment, nonresonant enclosure 3415 is a metal enclosure and comprises a metal top endpiece 3406 and a metal bottom endpiece 3408 with removable metal walls on four sides.

A sensor opening 3410 is provided for a temperature sensor which in the prototype embodiment was an infrared temperature sensor. The opening enables temperature measurements to be made without affecting the microwave field during operation.

Enclosure 3415 includes a sample opening 3420 that enables a sample to be inserted and/or removed. The height of the opening is adjustable by adjusting the distance between two plate holders 3416 and 3418.

A adjuster knob 3414 enables an operator to adjust the distance between plate holders 3416 and 3418 by turning knob 3414.

A microwave source (not shown) may be connected to coaxial connector 3412.

Figure 34B:
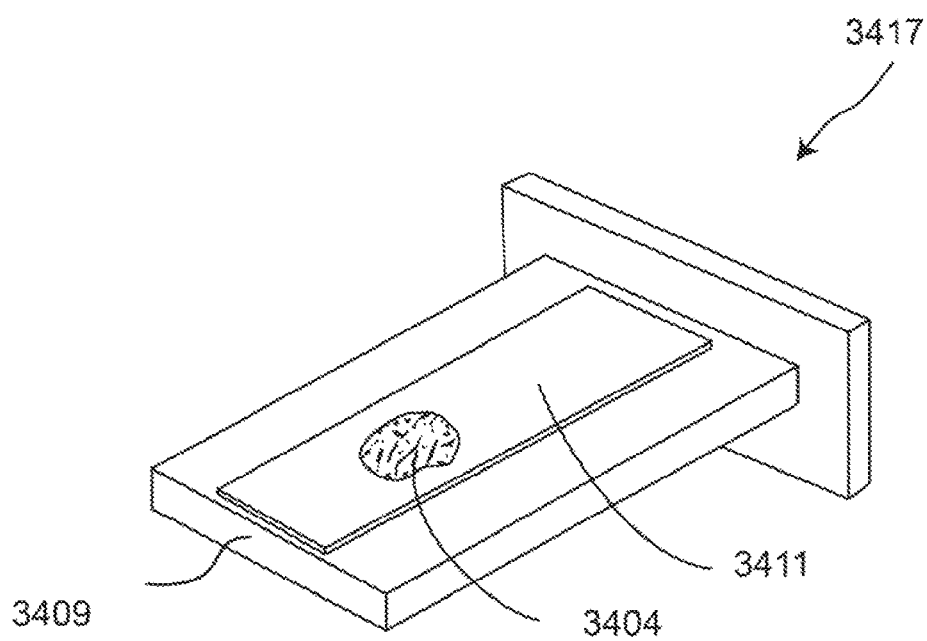
FIG. 34B depicts a sample rack, sample carrier and sample.

FIG. 34B illustrates an embodiment of a sample rack 3417 with a holder 3409 that is adapted to hold a sample carrier 3411, e.g. a microscope slide comprising a sample 3404. The sample rack 3417 may be inserted into sample opening 3420 shown in FIG. 34A to position the sample to be heated. Sample rack 3417 is depicted carrying a single sample carrier, e.g. microscope slide, but alternative embodiments may include multiple racks each with one sample carrier or one rack with multiple sample carriers. In embodiments adapted to accommodate multiple sample carriers in one or more racks, appropriate modification of the plate size, enclosure size, connectors, etc., may be may to accommodate the desired configuration.

Figure 34C:
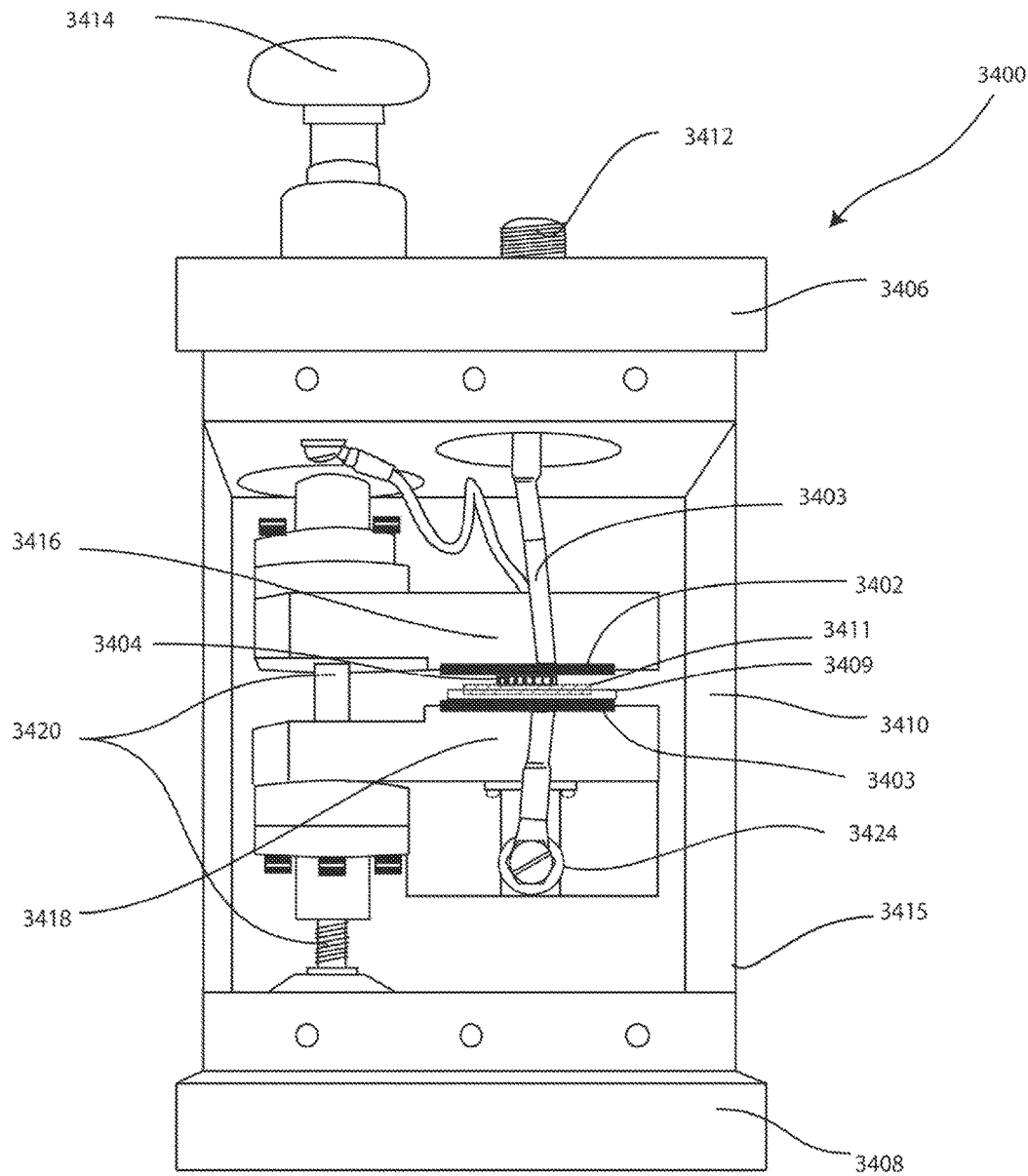
FIG. 34C illustrates a back view of an embodiment of a microwave heating system.

FIG. 34C depicts a back view of the embodiment of the microwave heating system 3400 which is shown In FIG. 34A from a front view. In FIG. 34C, one of the enclosure walls which would be normally screwed down has been removed in order to show the various internal components. The distance between top plate holder 3416 and bottom plate holder 3418 may be adjusted by turning adjuster knob 3414 which turns screw 3420 to cause threaded plate holders 3416 and 3418 to move up or down upon the threads of screw 3420.

An embodiment of a microwave applicator comprises top plate 3402 and bottom plate 3403. Top plate 3402 connects to one terminal of connector 3412 and a bottom plate 3403 connects coaxial connector 3424 which connects in turn to the other terminal of connector 3412. A microwave source may connect to connector 3412 to provide microwave energy for the applicator. Sample holder 3409 that holds a sample carrier 3411 carrying a sample 3404 may be inserted between plates 3402 and 3403.

Certain features of the embodiment of FIGS. 34A, 34B and 34C are adapted to facilitate prototype usage. However similar features such as adjustable plate distances, temperature sensor opening 3410 and removable walls of enclosure 3415 may also be included in any combination or arrangement for any desired embodiment of non-modal interplate microwave heating system.

Thus, various embodiments provide a microwave heating system having a non-modal interplate microwave applicator surrounding a load. The applicator may be position within a nonresonant enclosure that may act as a shield without creating mode patterns, standing waves, or other interferences. The applicator is formed from either a single-ended or a balanced pair of non-modal applicator plates wherein the electric field is propagated inward between the plates. The microwave heating according to the various embodiments provides a uniform energy distribution within the applicator structure.

What is claimed is:

1. A method of processing a biological sample on a microscope slide, the method comprising:
    positioning the biological sample between two plates of a non-modal interplate microwave applicator;
    connecting a microwave source to the non-modal interplate microwave applicator;
    generating an electromagnetic field between the two plates to apply to the biological sample on the microscope slide; and
    heating the sample to perform at least one processing step.

2. The method of claim 1, further comprising:
    monitoring a characteristic of the biological sample; and
    adjusting the electromagnetic field between the two plates in response at least in part to the monitoring.

3. The method of claim 2, wherein monitoring the characteristic of the sample comprises at least one of monitoring a temperature, a pressure, and a light scattering of the biological sample on the microscope slide.

4. The method of claim 1, wherein the at least one processing step is a pretreatment step chosen from baking, dewaxing, target retrieval, blocking, denaturation, enzymatic digestion, and any combination thereof.

5. The method of claim 1, wherein the at least one processing step is an incubation step chosen from histochemical incubation, immunohistochemical incubation, and in situ hybridization.

6. The method of claim 1, wherein the biological sample is processed for histochemical, immunohistochemical, or in situ hybridization analysis.

7. The method of claim 1, wherein a strength of the electromagnetic field does not depend on standing wave modes in the electromagnetic field.

8. The method of claim 1, wherein the electromagnetic field is a non-modal electromagnetic field.

9. The method of claim 1, wherein the non-modal interplate microwave applicator comprises a closed-loop single-ended applicator or a balanced applicator.

10. The method of claim 1, wherein the non-modal interplate microwave applicator comprises an impedance matched applicator.

11. The method of claim 1, wherein the two plates are applicator plates and a distance between the two plates is adjustable.

12. The method of claim 1, wherein a space between the two plates is at least partially filled with a dielectric material other than the biological sample.

13. The method of claim 1, further comprising:
    positioning a nonresonant enclosure to at least partially enclose the non-modal interplate microwave applicator.

14. The method of claim 13, wherein the nonresonant enclosure is made from at least one of a conducting material and a semiconducting material.

15. The method of claim 1, further comprising:
    positioning a supporting structure to engage the two plates of the non-modal interplate microwave applicator to secure the biological sample on the microscope slide, wherein the microscope slide is positioned between the two plates.

16. The method of claim 15, wherein the supporting structure comprises at least one material chosen from a microwave transparent material and a partially microwave transparent material.

* * * * *